US009216179B2

(12) United States Patent
Miner et al.

(10) Patent No.: US 9,216,179 B2
(45) Date of Patent: Dec. 22, 2015

(54) TREATMENT OF GOUT AND HYPERURICEMIA

(75) Inventors: Jeffrey Miner, San Diego, CA (US); Jean-Luc Girardet, San Diego, CA (US); Barry D. Quart, Encinitas, CA (US)

(73) Assignee: ARDEA BIOSCIENCES, INC., San Diego, CA (US)

( * ) Notice: Subject to any disclaimer, the term of this patent is extended or adjusted under 35 U.S.C. 154(b) by 48 days.

(21) Appl. No.: 13/704,192

(22) PCT Filed: Jun. 14, 2011

(86) PCT No.: PCT/US2011/040398
§ 371 (c)(1),
(2), (4) Date: Mar. 8, 2013

(87) PCT Pub. No.: WO2011/159732
PCT Pub. Date: Dec. 22, 2011

(65) Prior Publication Data
US 2013/0178484 A1   Jul. 11, 2013

Related U.S. Application Data

(60) Provisional application No. 61/489,420, filed on May 24, 2011, provisional application No. 61/430,522, filed on Jan. 6, 2011, provisional application No. 61/411,449, filed on Nov. 8, 2010, provisional application No. 61/355,004, filed on Jun. 15, 2010.

(51) Int. Cl.
*A61K 31/41* (2006.01)
*A61K 31/425* (2006.01)
*A61K 31/519* (2006.01)
*A61K 31/4196* (2006.01)
*A61K 31/426* (2006.01)
*A61K 45/06* (2006.01)

(52) U.S. Cl.
CPC .......... *A61K 31/519* (2013.01); *A61K 31/4196* (2013.01); *A61K 31/426* (2013.01); *A61K 45/06* (2013.01)

(58) Field of Classification Search
CPC ............ A61K 31/4196; A61K 31/426; A61K 31/519; A61K 45/06
USPC ............... 514/262.1, 365, 366, 367, 383, 384
See application file for complete search history.

(56) References Cited

U.S. PATENT DOCUMENTS

| 7,435,752 | B2 | 10/2008 | Girardet et al. |
| 7,547,680 | B2 | 6/2009 | Kikuchi et al. |
| 7,683,087 | B2 | 3/2010 | Girardet et al. |
| 8,003,681 | B2 | 8/2011 | Girardet et al. |
| 8,084,483 | B2 | 12/2011 | Quart et al. |
| 8,106,205 | B2 | 1/2012 | Girardet et al. |
| 8,173,690 | B2 * | 5/2012 | Gunic et al. ............... 514/384 |
| 8,193,234 | B2 | 6/2012 | Gunic et al. |
| 8,242,154 | B2 * | 8/2012 | Gunic et al. ............... 514/384 |
| 8,283,369 | B2 | 10/2012 | Quart et al. |
| 8,357,713 | B2 | 1/2013 | Quart et al. |
| 8,481,581 | B2 | 7/2013 | Girardet et al. |
| 8,546,437 | B2 | 10/2013 | Quart et al. |
| 8,552,043 | B2 | 10/2013 | Girardet et al. |
| 8,633,232 | B2 * | 1/2014 | Gunic et al. ............... 514/384 |
| 2006/0189811 | A1 | 8/2006 | Nakamura et al. |
| 2006/0270725 | A1 | 11/2006 | Girardet et al. |
| 2008/0176850 | A1 | 7/2008 | Girardet et al. |
| 2009/0197825 | A1 | 8/2009 | Quart et al. |
| 2010/0056465 | A1 | 3/2010 | Gunic et al. |
| 2010/0056542 | A1 | 3/2010 | Gunic et al. |
| 2010/0081827 | A1 | 4/2010 | Girardet et al. |
| 2010/0160351 | A1 | 6/2010 | Jenkins et al. |
| 2011/0190491 | A1 | 8/2011 | Girardet et al. |
| 2011/0268801 | A1 | 11/2011 | Girardet et al. |
| 2011/0293719 | A1 | 12/2011 | Girardet et al. |
| 2012/0122780 | A1 * | 5/2012 | De La Rosa et al. ........ 514/10.8 |
| 2012/0129903 | A1 | 5/2012 | Zamansky et al. |
| 2012/0164222 | A1 | 6/2012 | Quart et al. |
| 2012/0172405 | A1 | 7/2012 | Galvin et al. |
| 2013/0040963 | A1 | 2/2013 | Gunic et al. |
| 2013/0059868 | A1 * | 3/2013 | Miner et al. ............... 514/262.1 |
| 2013/0296345 | A1 * | 11/2013 | Quart ............................ 514/262.1 |
| 2013/0331403 | A1 | 12/2013 | Treiber et al. |
| 2013/0345271 | A1 | 12/2013 | Zamansky et al. |

(Continued)

FOREIGN PATENT DOCUMENTS

| CA | 2675443 | 7/2008 |
| CA | 2706858 | 6/2009 |

(Continued)

OTHER PUBLICATIONS

Fleishmann, R., et al. "Lesinurad (RDEA594), A Novel Uricosuric Agent, in Combination with Febuxostat Shows Significant Additive Urate Lowering Effects in Gout Subjects with 100% Response Achieved for all Combination Dose Regimens," Annual European Congress of Rheumatology EULAR, London, May 25-28, 2011.

Kerr, B., et al. "Pharmacokinetics, Efficacy and Safety of Lesinurad, A Novel URAT1 Inhibitor, In Individuals with Mild to Moderate Renal Impairment," American College of Rheumatology Annual General Meeting, Nov. 5-9, 2011, Chicago.

Kerr, B., et al. "Pharmacokinetics and Serum Urate Lowering Effect of RDEA594, A Novel URAT1 Inhibitor, In Gout Patients and Subjects with Varying Degrees of Renal Impairment," ASCPT American Society for Clinical Pharmacology and Therapeutics Annual Meeting, Dallas, Mar. 2-5, 2011.

(Continued)

*Primary Examiner* — My-Chau T Tran
(74) *Attorney, Agent, or Firm* — Wilson Sonsini Goodrich & Rosati

(57) ABSTRACT

Sodium 2-(5-bromo-4-(4-cyclopropylnaphthalen-1-yl)-4H-1,2,4-triazol-3-ylthio)acetate is described. In addition, pharmaceutical compositions and uses of such compositions for the treatment of a variety of diseases and conditions are described.

4 Claims, 8 Drawing Sheets

(56) References Cited

U.S. PATENT DOCUMENTS

| | | |
|---|---|---|
| 2014/0005136 A1 | 1/2014 | Quart et al. |
| 2014/0128338 A1 | 5/2014 | Gunic et al. |
| 2014/0171424 A1 | 6/2014 | Miner |
| 2015/0105410 A1* | 4/2015 | Treiber et al. ............. 514/262.1 |

FOREIGN PATENT DOCUMENTS

| | | |
|---|---|---|
| EP | 2266966 | 12/2010 |
| WO | WO-2006-026356 | 3/2006 |
| WO | WO-2009-070740 | 6/2009 |
| WO | WO-2010-028190 | 3/2010 |
| WO | WO-2011-085009 | 7/2011 |
| WO | WO-2011-126852 | 10/2011 |

OTHER PUBLICATIONS

Lasko, B., et al. "RDEA594, a Novel Uricosuric Agent, Significantly Reduced Serum Urate Levels and Was Well Tolerated in a Phase 2a Pilot Study in Hyperuricemic Gout Patients," ACR-ARHP Annual Scientific Meeting, Oct. 16-21, 2009, Philadelphia, CA USA.

Perez-Ruiz, F., et al. "Efficacy and Safety of Lesinurad (RDEA594), a Novel URAT1 Inhibitor, in Combination with Allopurinol in Gout Patients with an Inadequate Response to Allopurinol: Results from a Randomized, Blinded. Placebo-Controlled, Phase 2B Extension Study," Annual European Congress of Pheumatology EULAR, Berlin, Jun. 6-9, 2012.

Perez-Ruiz, F., et al. "Efficacy and Safety of Lesinurad (RDEA594), A Novel Uricosuric Agent, Given in Combination with Allopurinol in Allopurinol-Refractory Gout Patients: Randomized, Double-Blind Placebo-Controlled, Phase 2B Study [Preliminary Results]" Annual European Congress of Rheumatology EULAR 2011, May 25-28, 2011, London.

Perez-Ruiz, F., et al. "Efficacy and Safety of a Range of Doses of RDEA594, a Novel Uricosuric Agent, as Monotherapy in Gout Patients: Randomized, Double-Blind, Placebo-Controlled, Phase 2 Experience," Annual European Congress of Rheumatology EULAR 2010, Jun. 16-19, 2010, Rome.

Perez-Ruiz, F., et al. "Efficacy and Safety of RDEA594, a Novel Uricosuric Agent, as Combination Therapy with Allopurinol in Gout Patients: Randomized, Double-Blind, Placebo-Controlled, Phase 2 Experiences," Annual European Congress of Rheumatology EULAR 2010, Rome, Italy, Jun. 16-19, 2010.

Shen, Z., et al. "RDEA594, A Novel Uricosuric Agent, Shows Significant Additive Activity in Combination with Allopurinol in Gout Patients" ASCPT American Society of Clinical Pharmacology and Therapeutics Annual Meeting, Dallas, Mar. 2-5, 2011.

Sundy, J., et al. "Efficacy and Safety of Lesinurad (RDEA594), A Novel Uricosuric Agent, Given in Combination with Allopurinol in Allopurinol-Refractory Gout Patients: Preliminary Results from the Randomized, Blinded, Placebo-Controlled, Phase 2B Extension Study," American Collage of Pheumatology Annual General Meeting, Nov. 9-11, 2011, Chicago.

Tan, P.K., et al. "Lesinurad (RDEA594), A Investigational Uricosuric Agent for Hyperuricemia and Gout, Blocks OAT4 Transport, Mechanism of Hydrocholorothiazide-Dependant Hyperuricemia," Annual European Congress of Rheumatology EULAR, London, May 25-28, 2011.

Yang, X., et al. "Evaluation of Drug-Drug Interaction Potential Between RDEA594, Allopurinol and Febuxostat in Preclinical Species" 2009 ACR-ARHP Annual Scientific Meeting, Oct. 16-21, 2009, Philadelphia, PA, USA.

Yeh, L., et al. "RDEA594, a Novel Uricosuric Agent, Shows Impressive Reductions in Serum Urate Levels as a Monotherapy and Substantial Additive Activity in Combination with Febuxostat in Normal Healthy Volunteers," Annaul European Congress of Rheumatology EULAR 2010, Rome, Italy, Jun. 16-19, 2010.

Yeh, L., et al. "RDEA594, a Potential Uric Acid Lowering Agent through Inhibition of Uric Acid Reuptake, Shows Better Pharmacokinetics than its Prodrug RDEA806," 2008 ACR/ARHP Annual Scientific Meeting, Oct. 24-29, 2008, San Francisco, CA, USA.

Yeh, L., et al. "A Novel URAT1 Inhibitor, Shows Significant Additive Urate Lowering Effects in Combination with Febuxostat in Both Healthy Subjects and and Gout Patients," ASCPT American Society for Clinical Pharmacology and Therapeutics Annual Meeting, Dallas, Mar. 2-5, 2011.

Yeh, L., et al., "Lesinurad (RDEA594), A Novel URAT1 Inhibitor, Shows Additive Serum Urate Lowering Effects in Combination with Xanthine Oxidase Inhibitor Febuxostat" International Society for the Study of Xenobiotics, 4th Asia Pacific ISSX Meeting, Apr. 22-25, 2011.

Yeh, L.T., et al. "Mode of Action of RDEA594 as a Uric Acid Lowering Agent in Humans Following Multiple Doses of its Prodrug, RDEA806," Annual European Congress of Rheumatology EULAR 2008, Paris, France, Jun. 11-14, 2008.

Yeh, L.T., et al. "Safety, Pharmacokinetics, and Serum Uric Acid Lowering Effect of RDEA594, A Novel, Uricosuric Agent, in Healthy Volunteers," Annual European Congress of Rheumatology EULAR 2009, Copenhagen, Denmark, Jun. 10-13, 2009.

Yeh, L-T., et al. "RDEA594: A Potent URAT1 Inhibitor Without Affecting Other Important Renal Transporters, OAT1 and OAT3," Annual European Congress of Rheumatology EULAR 2009, Copenhagen, Denmark, Jun. 10-13, 2009.

PCT/US11/040398 International Search Report and Written Opinion dated Nov. 1, 2011.

PCT/US11/030364 International Search Report and Written Opinion dated Nov. 10, 2011.

Schumacher, H.R., Jr. "Febuxostat: a Non-Purine, Selective Inhibitor of Xanthine Oxidase for the Management of Hyperuricaemia in Patients with Gout," Expert Opin Investig Drugs 14(7):893-903 (2005).

Burn, C.M. and Wortmann, R.L., "Gout Therapeutics: New Drugs for an Old Disease," Lancet 377(9760): 165-177 (Jan. 8, 2011) (Published Online. Aug. 17, 2010).

Becker, M.A., et al., "Febuxostat Compared with Allopurinol in Patients with Hyperuricemia and Gout," The New England Journal of Medicine 353(23):2450-2461 (Dec. 8, 2005).

PRNewswire, "Ardea Biosciences Reports Positive Results for RDEA594, its Lead Product Candidate for Gout, in Combination with Allopurinol or Febuxostat," Jan. 7, 2009.

PRNewswire, "Ardea Biosciences Reports Positive Results for RDEA594, its Lead Product Candidate for Gout, in Combination with Allopurinol or Febuxostat," Jan. 7, 2010.

PRNewswire, "Ardea Biosciences Announces Positive Top-Line Results From a Phase 2b Study of RDEA594 Given as Monotherapy in the Treatment of Hyperuricemia in Gout Patients," Mar. 31, 2010.

Ardea Bioscience Company Update. http://www.getfilings.com/sec-filings/091019/Ardea-Biosciences-Inc-DE__8-K/a54060exv99w1.htm (2009).

Co-pending U.S. Appl. No. 14/559,803, filed Dec. 3, 2014.
Co-pending U.S. Appl. No. 14/577,129, filed Dec. 19, 2014.
Li. Gout: a review of its aetiology and treatment. Hong Kong Med J. 10(4):261-270 (2004).
U.S. Appl. No. 13/637,343 Office Action dated Jan. 2, 2015.
U.S. Appl. No. 13/879,373 Office Action dated May 8, 2015.

* cited by examiner

IL-1ra = rilonacept

IL-1ra = rilonacept

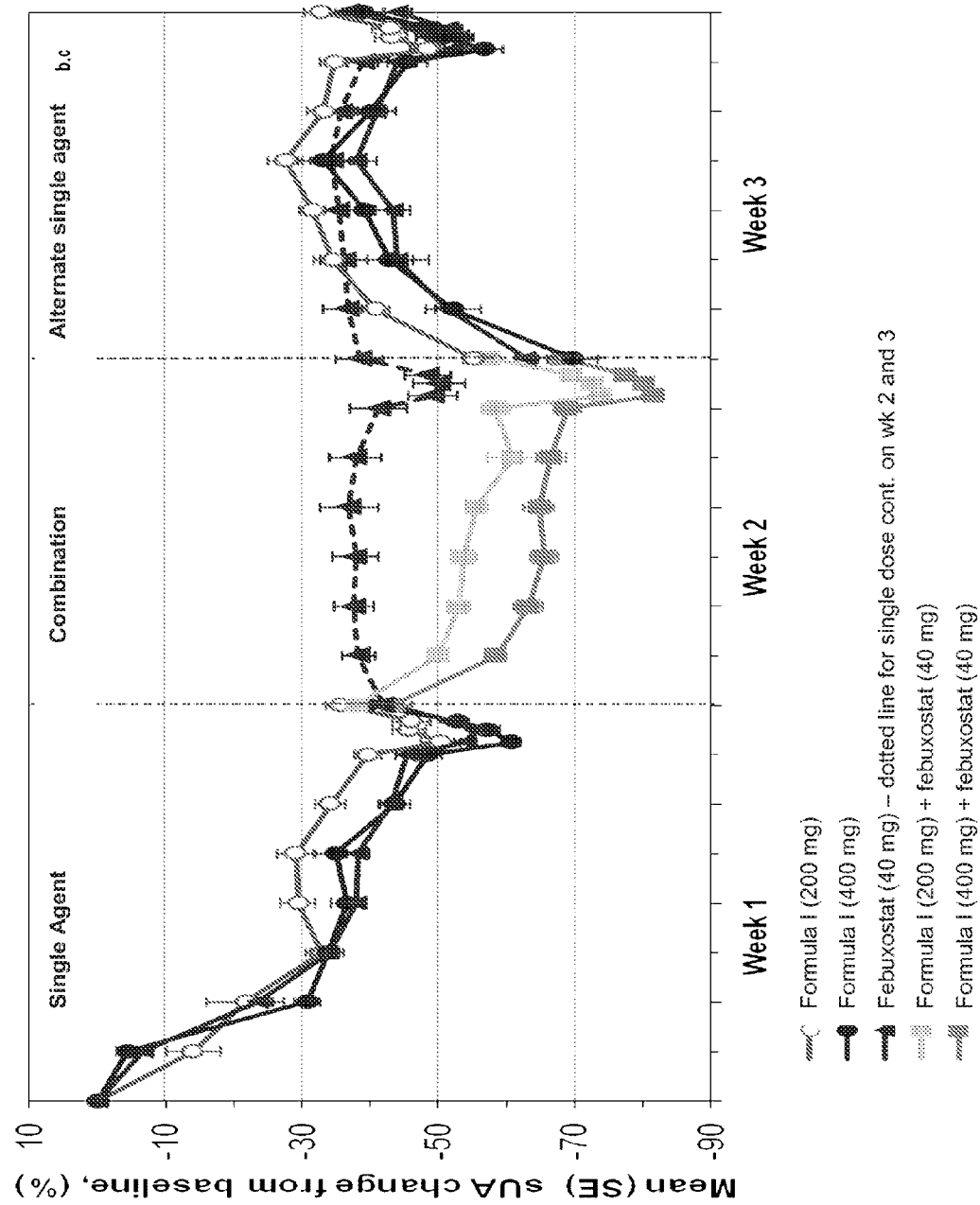

TREATMENT OF GOUT AND HYPERURICEMIA

CROSS-REFERENCE

This application is filed pursuant to 35 U.S.C. §371 as a United States National Phase Application of International Application Ser. No. PCT/US11/40398, filed Jun. 14, 2011, which claims priority to U.S. Provisional Application 61/355,004, filed Jun. 15, 2010, U.S. Provisional Application 61/411,449, filed Nov. 8, 2010, U.S. Provisional Application 61/430,522, filed Jan. 6, 2011, and U.S. Provisional Application 61/489,420, filed May 24, 2011, which are each incorporated herein in their entirety by reference.

FIELD OF THE INVENTION

The present invention relates to the treatment of gout and methods of reducing uric acid levels.

BACKGROUND OF THE INVENTION

Gout is a painful, debilitating and progressive disease caused by abnormally elevated levels of uric acid in the blood stream. Gout is associated with elevated levels of uric acid that crystallize and deposit in joints, tendons, and surrounding tissues. Gout is marked by recurrent attacks of red, tender, hot, and/or swollen joints. This leads to the deposition of painful, needle-like uric acid crystals in and around the connective tissue of the joints and in the kidneys, resulting in inflammation, the formation of disfiguring nodules, intermittent attacks of severe pain and kidney damage. In addition, evidence suggests that the chronic elevation of uric acid associated with gout, known as hyperuricemia, may also have systemic consequences, including an increased risk for kidney dysfunction and cardiovascular disease.

In 2008, approximately 8.3 million patients in the U.S., 6.4 million patients in the European Union and 2.9 million patients in Japan were diagnosed with gout. Gout is the most common form of inflammatory arthritis in men over the age of 40 and represents a significant unmet medical need with limited treatment options.

SUMMARY OF THE INVENTION

In certain embodiments, provided herein are methods and compositions for the reduction of serum uric acid levels (sUA) or the treatment of gout in individuals in need thereof. In some embodiments, such compositions comprise and such methods comprise the administration to an individual in need thereof an effective amount of a compound of formula I:

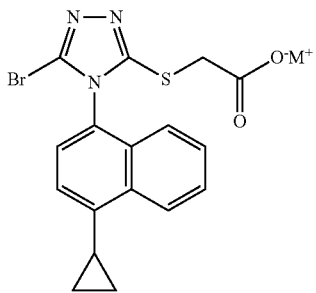

formula (I)

In specific embodiments, the compound of formula I is 2-(5-bromo-4-(4-cyclopropylnaphthalen-1-yl)-4H-1,2,4-triazol-3-ylthio)acetate, or a polymorph thereof, or a pharmaceutically acceptable salt of 2-(5-bromo-4-(4-cyclopropyl-naphthalen-1-yl)-4H-1,2,4-triazol-3-ylthio)acetate or a polymorph thereof. In more specific embodiments, M+ is H+, Na+ or K+.

Provided in certain embodiments herein is a method of treating gout and/or gout flares comprising administering to an individual an effective amount of a compound of formula I. In some embodiments, the method comprises administering to the individual an effective amount of a compound of formula I and an effective amount of colchicine. In certain embodiments, the method comprises administering to the individual an effective amount of a compound of formula I and an effective amount of a xanthine oxidate (XO) inhibitor (e.g., allopurinol or febuxostat). In some embodiments, the method comprises administering to the individual an effective amount of a compound of formula I, an effective amount of colchicine, and an effective amount of a xanthine oxidate (XO) inhibitor (e.g., allopurinol or febuxostat). In specific embodiments, provided herein is a method of treating gout and/or gout flares in an individual suffering from renal impairment (e.g., moderate renal impairment).

Provided in some embodiments herein is a method of reducing serum uric acid levels (including, e.g., in a method of treating gout and/or gout flares) in an individual in need thereof, the method comprising administering to the individual an effective amount of a compound of formula I. In further embodiments, the method further comprises administering to the individual (i) an effective amount of colchicine, (ii) an effective amount of a xanthine oxidate (XO) inhibitor, or (iii) a combination thereof. In certain embodiments, provided herein is a method of reducing high baseline serum uric acid levels in an individual, the method comprising administering to the individual an effective amount of a compound of formula I and a xanthine oxidate (XO) inhibitor (e.g., allopurinol or febuxostat). In specific embodiments, a high baseline serum uric acid level is >10 mg/dL, >9.5 mg/dL, >9 mg/dL, >8.5 mg/dL, >8 mg/dL, or the like. In specific embodiments, such methods comprise reducing the serum uric acid levels to less <6.5 mg/dL, <6.4 mg/dL, <6.3 mg/dL, <6.2 mg/dL, <6.1 mg/dL, <6 mg/dL, <5.9 mg/dL, <5.8 mg/dL, <5.7 mg/dL, <5.6 mg/dL, <5.5 mg/dL, <5.4 mg/dL, <5.3 mg/dL, <5.2 mg/dL, <5.1 mg/dL, <5 mg/dL or the like. In some embodiments, a method of reducing serum uric acid levels described herein comprises providing an intraday reduction of serum uric acid levels of >40%, >45%, >50%, >55%, >60%, >65%, >70%, >75%, >80%, or more.

Provided in specific embodiments herein is a method of treating tophaceous gout.

In some embodiments, any method described herein that comprises the administration of a first agent and a second agent comprises the initial administration of one agent (e.g., for one day, two days, three days, one week, two weeks, one month, two months, three months, or the like), such as an XO inhibitor or compound of formula I, followed by the administration of another agent involved in the therapy (or a combination of a first and second agent as described herein), such as a compound of formula I or an XO inhibitor (or both).

In certain instances, the treatment of gout involves the reduction of serum uric acid levels. However, gout flares are associated with the reduction of uric acid levels. Drugs such as colchicine can reduce the pain associated with gout flares while a patient's serum uric acid levels are being reduced, however, colchicine is associated with several undesired side effects, including gastrointestinal disorders.

Described in certain embodiments herein are methods, compositions and dosing regimens for reducing serum uric acid levels while providing for a concomitant reduction in the intensity and duration of gout flares associated with other gout medications. Furthermore, described herein are methods, compositions and dosing regimens for weaning a patient off of co-administered colchicine; such weaning includes lower doses of colchicine and less time on colchicine relative to other gout medications.

Some embodiments described herein provide a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and colchicine to a subject, wherein said method provides greater mean gout flare reduction than co-administration of colchicine and therapeutic agent that is not a dual inhibitor of URAT1 and an inflammasome.

Other embodiments provided herein describe a method wherein the total dosage of colchicine administered during co-administration with 2-(5-bromo-4-(4-cyclopropylnaphthalen-1-yl)-4H-1,2,4-triazol-3-ylthio)acetate, or a pharmaceutically acceptable salt thereof, is at least 50% less than the total dosage of colchicine co-administered with a therapeutic agent that is not a dual inhibitor of URAT1 and an inflammasome.

Some embodiments provide the method wherein the amount of time that colchicine is co-administered with 2-(5-bromo-4-(4-cyclopropylnaphthalen-1-yl)-4H-1,2,4-triazol-3-ylthio)acetate, or a pharmaceutically acceptable salt thereof, is at least one week less than when colchicine is co-administered with a therapeutic agent that is not a dual inhibitor of URAT1 and an inflammasome.

Other embodiments provided herein describe a method of reducing the duration of gout flares comprising administration of a pharmaceutical composition comprising 2-(5-bromo-4-(4-cyclopropylnaphthalen-1-yl)-4H-1,2,4-triazol-3-ylthio)acetate, or a pharmaceutically acceptable salt thereof, to a subject, wherein the mean duration of the gout flares in a patient undergoing uric acid level reduction is less than four days. Certain embodiments provided herein describe the method, wherein the mean duration of the gout flares is less than three days. In specific embodiments, the mean duration of the gout flares is less than two days.

Also provided in certain embodiments herein are methods for treating gout comprising administration to a patient in need a therapeutic agent that is a dual inhibitor of URAT1 and inflammasome. In specific embodiments, the dual inhibitor of URAT1 and inflammasome is 2-(5-bromo-4-(4-cyclopropylnaphthalen-1-yl)-4H-1,2,4-triazol-3-ylthio)acetate, or a polymorph thereof, or a pharmaceutically acceptable salt of 2-(5-bromo-4-(4-cyclopropylnaphthalen-1-yl)-4H-1,2,4-triazol-3-ylthio)acetate or a polymorph thereof.

Some embodiments described herein provide a method of reducing monosodium urate induced inflammation comprising administering a pharmaceutical composition comprising a pharmaceutical agent having both uricosuric and anti-inflammatory activity. In certain embodiments, the pharmaceutical agent is a URAT1 inhibitor with anti-inflammatory activity. In certain specific embodiments, the pharmaceutical agent is 2-(5-bromo-4-(4-cyclopropylnaphthalen-1-yl)-4H-1,2,4-triazol-3-ylthio)acetate, or a pharmaceutically acceptable salt thereof.

Certain embodiments described herein provide the method wherein the daily dose of 2-(5-bromo-4-(4-cyclopropylnaphthalen-1-yl)-4H-1,2,4-triazol-3-ylthio)acetate, or a pharmaceutically acceptable salt thereof, is about 750 mg. In some embodiments, the daily dose of 2-(5-bromo-4-(4-cyclopropylnaphthalen-1-yl)-4H-1,2,4-triazol-3-ylthio)acetate, or a pharmaceutically acceptable salt thereof, is about 600 mg. In other embodiments, the daily dose of 2-(5-bromo-4-(4-cyclopropylnaphthalen-1-yl)-4H-1,2,4-triazol-3-ylthio)acetate, or a pharmaceutically acceptable salt thereof, is about 500 mg. In certain embodiments, the daily dose of 2-(5-bromo-4-(4-cyclopropylnaphthalen-1-yl)-4H-1,2,4-triazol-3-ylthio)acetate, or a pharmaceutically acceptable salt thereof, is about 400 mg. In certain embodiments, the daily dose of 2-(5-bromo-4-(4-cyclopropylnaphthalen-1-yl)-4H-1,2,4-triazol-3-ylthio)acetate, or a pharmaceutically acceptable salt thereof, is about 200 mg.

In some embodiments, the daily dose is administered orally. In other embodiments, the daily dose is administered in the morning. In certain embodiments, the daily dose is administered with food.

Provided in certain embodiments herein is a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and febuxostat to a subject. In other embodiments, provided herein are methods of reducing serum uric acid levels in a human comprising co-administration of 2-(5-bromo-4-(4-cyclopropylnaphthalen-1-yl)-4H-1,2,4-triazol-3-ylthio)acetate, or a pharmaceutically acceptable salt thereof, and febuxostat to a subject. In some embodiments, provided herein is a method of treating hyperuricemia in a human comprising co-administration of 2-(5-bromo-4-(4-cyclopropylnaphthalen-1-yl)-4H-1,2,4-triazol-3-ylthio)acetate, or a pharmaceutically acceptable salt thereof, and febuxostat to a subject. In certain embodiments, provided herein is a method of treating hyperuricemia in a human with gout comprising co-administration of 2-(5-bromo-4-(4-cyclopropylnaphthalen-1-yl)-4H-1,2,4-triazol-3-ylthio)acetate, or a pharmaceutically acceptable salt thereof, and febuxostat to a subject. In other embodiments, provided herein is a method of treating or preventing a condition characterized by abnormal tissue or organ levels of uric acid in an individual comprising co-administration of 2-(5-bromo-4-(4-cyclopropylnaphthalen-1-yl)-4H-1,2,4-triazol-3-ylthio)acetate, or a pharmaceutically acceptable salt thereof, and febuxostat to a subject. In various embodiments, any such method provides any therapeutic effect described herein (e.g., for combination therapies including the co-administration of 2-(5-bromo-4-(4-cyclopropylnaphthalen-1-yl)-4H-1,2,4-triazol-3-ylthio)acetate, or a pharmaceutically acceptable salt thereof, and febuxostat), such as, by way of non-limiting example, provides:

a. serum urate levels of less than 6 mg/dL;
   b. serum urate levels of less than 5 mg/dL;
   c. serum urate levels of less than 4 mg/dL;
   d. serum urate levels of less than 3 mg/dL;
   e. serum urate levels intraday change of more than 50%;
   f. serum urate levels intraday change of more than 60%; and/or
   g. or a combination thereof.

Provided in certain embodiments herein is a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject. In other embodiments, provided herein are methods of reducing serum uric acid levels in a human comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject. In some embodiments, provided herein is a method of treating hyperuricemia in a human comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject. In certain embodiments, provided herein is a method of treating hyperuricemia in a human with gout comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject. In other embodiments, provided herein is a method of treating or preventing a condition characterized by abnormal tissue or organ levels of uric acid in an individual comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject. In various embodiments, any such method provides any therapeutic effect described herein (e.g., for combination therapies including the co-administration of 2-(5-bromo-4-(4-cyclopropylnaphthalen-1-yl)-4H-1,2,4-triazol-3-ylthio)acetate, or a pharmaceutically acceptable salt thereof, and allopurinol), such as, by way of non-limiting example, provides:
  a. serum urate levels of less than 6 mg/dL;
  b. serum urate levels of less than 5 mg/dL;
  c. serum urate levels of less than 4 mg/dL;
  d. serum urate levels of less than 3 mg/dL;
  e. serum urate levels intraday change of more than 50%;
  f. serum urate levels intraday change of more than 60%;
  g. a mean change in serum urate levels of greater than 8%;
  h. adverse events in less than 15% of the subjects;
  i. a response rate (e.g., ITT analysis) of greater than 50%;
  j. or a combination thereof.

Certain embodiments provided herein describe the above listed methods of reducing the duration of gout flares further comprising administration of a second serum uric acid lowering agent. In some embodiments, the second serum uric acid lowering agent is a xanthine oxidase inhibitor. In specific embodiments, the xanthine oxidase inhibitor is febuxostat or allopurinol.

INCORPORATION BY REFERENCE

All publications and patent applications mentioned in this specification are herein incorporated by reference for the purposes cited.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 8 illustrates significant sUA lower effects observed after dosing with compound of Formula I and excellent additive effects in combination with febuxostat.

DETAILED DESCRIPTION OF THE INVENTION

Figure 1:
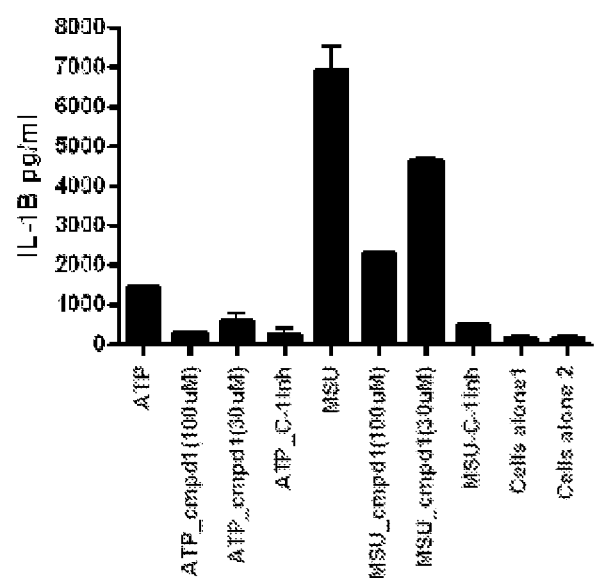
FIG. 1 illustrates the effect of sodium 2-(5-bromo-4-(4-cyclopropylnaphthalen-1-yl)-4H-1,2,4-triazol-3-ylthio)acetate on IL-1 production.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

The section headings used herein are for organizational purposes only and are not to be construed as limiting the subject matter described. All documents, or portions of documents, cited in the application including, without limitation, patents, patent applications, articles, books, manuals, and treatises are hereby expressly incorporated by reference in their entirety for any purpose.

The treatment of gout typically involves the reduction of serum uric acid levels. However, gout flares are associated with the reduction of uric acid levels. Drugs such as colchicine can reduce the pain associated with gout flares while a patient's serum uric acid levels are being reduced, however, colchicine is associated with several undesired side effects, including gastrointestinal disorders.

Accordingly, described herein in some embodiments are methods, compositions and dosing regimens for reducing serum uric acid levels while providing for a concomitant reduction in the intensity and duration of gout flares associated with other gout medications. Furthermore, described herein in other embodiments are methods, compositions and dosing regimens for weaning a patient off of co-administered colchicine; such weaning includes lower doses of colchicine and less time on colchicine relative to other gout medications.

Some embodiments described herein provide a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and colchicine to a subject, wherein said method provides greater mean gout flare reduction than co-administration of colchicine and therapeutic agent that is not a dual inhibitor of URAT1 and an inflammasome.

In certain embodiments, the total dosage of colchicine administered during co-administration with 2-(5-bromo-4-(4-cyclopropylnaphthalen-1-yl)-4H-1,2,4-triazol-3-ylthio)acetate, or a pharmaceutically acceptable salt thereof, is at least 30%, at least 35%, at least 38%, at least 40%, at least 42%, at least 45%, at least 48%, at least 50%, at least 52%, at least 55%, at least 57%, at least 60%, at least 62%, at least 65%, at least 67%, at least 70%, at least 72%, at least 75%, at least 77%, or at least 80% less than the total dosage of colchicine co-administered with a therapeutic agent that is not a dual inhibitor of URAT1 and an inflammasome. In specific embodiments, the total dosage of colchicine administered during co-administration with 2-(5-bromo-4-(4-cyclopropylnaphthalen-1-yl)-4H-1,2,4-triazol-3-ylthio)acetate, or a pharmaceutically acceptable salt thereof, is at least 50% less than the total dosage of colchicine co-administered with a therapeutic agent that is not a dual inhibitor of URAT1 and an inflammasome.

In other embodiments, the amount of time that colchicine is co-administered with 2-(5-bromo-4-(4-cyclopropylnaphthalen-1-yl)-4H-1,2,4-triazol-3-ylthio)acetate, or a pharmaceutically acceptable salt thereof, is at least one day, two days, three days, four days, five days, six days, one week, 1.5 weeks, 2 weeks, 2.5 weeks, 3 weeks, 3.5 weeks, 4 weeks, 4.5 weeks, 5 weeks, 5.5 weeks, 6 weeks, 6.5 weeks, 7 weeks, 8 weeks, 9 weeks or 10 weeks less than when colchicine is co-administered with a therapeutic agent that is not a dual inhibitor of URAT1 and an inflammasome. In certain specific embodiments, the amount of time that colchicine is co-administered with 2-(5-bromo-4-(4-cyclopropylnaphthalen-1-yl)-4H-1,2,4-triazol-3-ylthio)acetate, or a pharmaceutically acceptable salt thereof, is at least one week less than when colchicine is co-administered with a therapeutic agent that is not a dual inhibitor of URAT1 and an inflammasome.

Some embodiments provided herein describe a method of reducing the duration of gout flares comprising administration of a pharmaceutical composition comprising 2-(5-bromo-4-(4-cyclopropylnaphthalen-1-yl)-4H-1,2,4-triazol-3-ylthio)acetate, or a pharmaceutically acceptable salt thereof, to a subject, wherein the mean duration of the gout flares in a patient undergoing uric acid level reduction is less than 7, 6, 5, 4, 3, 2, or 1 day(s). Some embodiments provided herein describe a method of reducing the duration of gout flares comprising administration of a pharmaceutical composition comprising 2-(5-bromo-4-(4-cyclopropylnaphthalen-1-yl)-4H-1,2,4-triazol-3-ylthio)acetate, or a pharmaceutically acceptable salt thereof, to a subject, wherein the mean duration of the gout flares in a patient undergoing uric acid level reduction is less than four days. In certain embodiments, the mean duration of the gout flares is less than three days. In further or alternative embodiments, the mean duration of the gout flares is less than two days.

Other embodiments provided herein describe a method for treating gout comprising administration to a patient in need a therapeutic agent that is a dual inhibitor of URAT1 and inflammasome. In certain specific embodiments, the dual inhibitor of URAT1 and inflammasome is 2-(5-bromo-4-(4-cyclopropylnaphthalen-1-yl)-4H-1,2,4-triazol-3-ylthio)acetate, or a polymorph thereof, or a pharmaceutically acceptable salt of 2-(5-bromo-4-(4-cyclopropylnaphthalen-1-yl)-4H-1,2,4-triazol-3-ylthio)acetate or a polymorph thereof.

Certain embodiments provide a method of reducing monosodium urate induced inflammation comprising administering a pharmaceutical composition comprising a pharmaceutical agent having both uricosuric and anti-inflammatory activity. Certain specific embodiments provided herein describe the method wherein the pharmaceutical agent is a URAT1 inhibitor with anti-inflammatory activity. In specific embodiments, the pharmaceutical agent is 2-(5-bromo-4-(4-cyclopropylnaphthalen-1-yl)-4H-1,2,4-triazol-3-ylthio)acetate, or a pharmaceutically acceptable salt thereof.

In some embodiments, the daily dose of 2-(5-bromo-4-(4-cyclopropylnaphthalen-1-yl)-4H-1,2,4-triazol-3-ylthio)acetate, or a pharmaceutically acceptable salt thereof, is about 1000 mg, 950 mg, 900 mg, 875 mg, 850 mg, 825 mg, 800 mg, 775 mg, 750 mg, 725 mg, 700 mg, 675 mg, 650 mg, 625 mg, 600 mg, 575 mg, 550 mg, 525 mg, 500 mg, 475 mg, 450 mg, 425 mg, 400 mg, 375 mg, 350 mg, 325 mg, 300 mg, 275 mg, 250 mg, 225 mg, 200 mg, 175 mg, 150 mg, 125 mg, 100 mg, 75 mg, 50 mg, or 25 mg. In some embodiments, the daily dose of 2-(5-bromo-4-(4-cyclopropylnaphthalen-1-yl)-4H-1,2,4-triazol-3-ylthio)acetate, or a pharmaceutically acceptable salt thereof, is about 750 mg. In certain embodiments, the daily dose of 2-(5-bromo-4-(4-cyclopropylnaphthalen-1-yl)-4H-1,2,4-triazol-3-ylthio)acetate, or a pharmaceutically acceptable salt thereof, is about 600 mg. In other embodiments, the daily dose of 2-(5-bromo-4-(4-cyclopropylnaphthalen-1-yl)-4H-1,2,4-triazol-3-ylthio)acetate, or a pharmaceutically acceptable salt thereof, is about 500 mg. In further or alternative embodiments, the daily dose of 2-(5-bromo-4-(4-cyclopropylnaphthalen-1-yl)-4H-1,2,4-triazol-3-ylthio)acetate, or a pharmaceutically acceptable salt thereof, is about 400 mg. In still further or alternative embodiments, the daily dose of 2-(5-bromo-4-(4-cyclopropylnaphthalen-1-yl)-4H-1,2,4-triazol-3-ylthio)acetate, or a pharmaceutically acceptable salt thereof, is about 200 mg.

In some embodiments, the daily dose is administered orally. In certain embodiments, the daily dose is administered in the morning. In certain embodiments, the daily dose is administered in the afternoon. In certain embodiments, the daily dose is administered in the evening. In further or additional embodiments, the daily dose is administered with food. In further or alternative embodiments, the daily dose is administered without food.

In some embodiments, methods of reducing the duration of gout flares further comprise administration of a second serum uric acid lowering agent. In certain embodiments, the second serum uric acid lowering agent is a xanthine oxidase inhibitor. In certain specific embodiments, in the xanthine oxidase inhibitor is febuxostat or allopurinol.

Certain embodiments described herein provide a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and febuxostat to a subject, wherein said method provides serum urate levels of less than 7, less than 6.9, less than 6.8, less than 6.7, less than 6.6, less than 6.5, less than 6.4, less than 6.3, less than 6.2, less than 6.1, less than 6, less than 5.9, less than 5.8, less than 5.7, less than 5.6, less than 5.5, less than 5.4, less than 5.3, less than 5.2, less than 5.1, less than 5, less than 4.8, less than 4.5, less than 4, less than 3.5, less than 3, or less than 2.5 mg/dL. Certain specific embodiments described herein provide a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and febuxostat to a subject, wherein said method provides serum urate levels of less than 6 mg/dL.

In certain specific embodiments, the method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and febuxostat to a subject provides serum urate levels of less than 5 mg/dL.

In further or alternative embodiments, the method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and febuxostat to a subject provides serum urate levels of less than 4 mg/dL.

In further or alternative embodiments, the method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and febuxostat to a subject provides serum urate levels of less than 3 mg/dL.

Other embodiments described herein provide a method of treating gout comprising co-administration of 2-(5-bromo-4-(4-cyclopropylnaphthalen-1-yl)-4H-1,2,4-triazol-3-ylthio)

acetate, or a pharmaceutically acceptable salt thereof, and febuxostat to a subject, wherein said method provides serum urate levels intraday change of more than 80%, more than 75%, more than 70%, more than 65%, more than 60%, more than 58%, more than 55%, more than 53%, more than 50%, more than 48%, more than 45%, more than 43%, more than 40%, more than 35%, or more than 30%. In certain specific embodiments, the method provides serum urate levels intraday change of more than 50%.

Some embodiments described herein provide a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and febuxostat to a subject, wherein said method provides serum urate levels intraday change of more than 60%.

In some embodiments, the gout condition in the subject is characterized by the presence of large accumulated deposits of uric acid or tophi.

Some embodiments described herein provide a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject, wherein said method provides serum urate levels of less than 7, less than 6.9, less than 6.8, less than 6.7, less than 6.6, less than 6.5, less than 6.4, less than 6.3, less than 6.2, less than 6.1, less than 6, less than 5.9, less than 5.8, less than 5.7, less than 5.6, less than 5.5, less than 5.4, less than 5.3, less than 5.2, less than 5.1, less than 5, less than 4.8, less than 4.5, less than 4, less than 3.5, less than 3, or less than 2.5 mg/dL. In certain embodiments, the method provides serum urate levels of less than 6 mg/dL. In further or alternative embodiments, the method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject provides serum urate levels of less than 5 mg/dL.

In still further or alternative embodiments, the method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject provides serum urate levels of less than 4 mg/dL.

In even further or alternative embodiments, the method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject, provides serum urate levels of less than 3 mg/dL.

Other embodiments described herein provide a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject, wherein said method provides serum urate levels intraday change of more than 80%, more than 75%, more than 70%, more than 65%, more than 60%, more than 58%, more than 55%, more than 53%, more than 50%, more than 48%, more than 45%, more than 43%, more than 40%, more than 35%, or more than 30%. In certain embodiments, the method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject provides serum urate levels intraday change of more than 50%. In certain other embodiments, the method provides serum urate levels intraday change of more than 60%.

Gout

Gout is a painful form of arthritis caused by high uric acid in the blood (hyperuricemia). As serum uric acid (sUA) levels increase, so does the risk of having gout and painful flares. Decreasing uric acid (e.g., to a level of less than 6 mg/dL) has been shown to be effective for management of gout over the long-term.

According to the National Health and Nutrition Examination Survey III, 1988-1994, an estimated 5.1 million people in the United States suffer from gout. Gout is the most common form of inflammatory arthritis in men. Gout affects approximately 3 times as many men as women, and men are more likely than women to have gout at all ages. Racial and ethnic differences are not as distinct among patients in the US, though African Americans aged 45 years or older are more likely to have gout than Caucasians in the same age group.

Gout flares occur when excess uric acid forms crystals, causing inflammation in the joints that leads to swelling and pain. Flares happen most often in the toes, but can happen in hands, elbows, and knees. Gout flares often occur without warning and can cause joint swelling, severe pain, tenderness, redness, and heat. Over time, gout flares become more frequent and/or of greater duration.

Acute gout is caused by an inflammatory response to monosodium urate monohydrate (MSUM) crystal formation—a temperature-dependent phenomenon, which can occur under conditions of elevated serum urate concentration. Gout flare is known as one of the most painful conditions in rheumatology, with pain intensity comparable to childbirth or long bone fractures. The condition regularly interrupts sleep, inhibits walking, and interferes with work and leisure activities.

Serum urate, produced when purines are metabolized, is eliminated from the body in the form of uric acid. Uric acid may have a significant physiological function, acting as an antioxidant, a role in which it is as effective as ascorbate. However, when the balance of purine nucleotide synthesis, breakdown and recycling, and elimination becomes unbalanced, hyperuricemia results.

The development of hyperuricemia is straightforward: uric acid builds up in the blood when the body increases its production of uric acid, or the kidneys do not eliminate it efficiently, or both. Overproduction is responsible for 10% of cases of primary gout; underexcretion for 90%.

Production may increase through endogenous (cell turnover and metabolism) and/or exogenous (dietary) factors.

Reduced elimination suggests a renal cause because most uric acid is eliminated via the kidneys. (Enteric elimination is the next most significant means of elimination, and it can increase in response to hyperuricemia.) Genetic factors may play a role for individuals with hyperuricemia and reduced renal clearance of uric acid. Most subjects with gout have lower clearance rates for uric acid, which may be measured directly or as a ratio of urate to inulin clearance (Curate/Cinulin ratio). However, most gout and hyperuricemia patients show no other renal function abnormality.

Though 90% of primary gout cases are triggered by difficulties in urate elimination, the exact mechanism behind lower uric acid clearance rates has not been established. Known factors that may affect urate clearance include the volume of urine flow (excretion is increased by >25% if urine flow is doubled), the level of estrogens (as evidenced by lower serum uric acid concentrations in women before menopause and in children), surgery, and autonomic nervous system function.

Secondary gout is also attributed to a reduction in the glomerular filtration rate causing a decrease in the excretion of uric acid by the kidney. This is observed in certain kidney disorders or with medications such as diuretics that interfere with urate excretion.

Gout Flares

The serum urate saturation point is approximately 6.8 mg/dL. Although several biochemical factors impact whether an individual experiences a flare at this point, risk for the development of gout symptoms increases steadily at concentrations higher than 6 mg/dL. In some patients with hyperuricemia, urate crystallizes as monosodium urate monohydrate (MSUM) and forms deposits in the synovial membrane. An acute gout attack occurs when there is a marked inflammatory response to these crystal deposits.

In broad terms, gout attacks are symptoms of the inflammatory response to monosodium urate crystal deposition. Supersaturation of serum urate is the underlying cause, but not sufficient in and of itself to cause precipitation. Similarly, the presence of crystals alone may be insufficient to elicit an inflammatory response.

Asymptomatic patients may have crystals in the synovial fluid and neutrophils within the synovium—diagnostic clinical signs of gout. Additionally, microtophi have been identified in areas of the synovium during the early stages of gout attacks. These observations are consistent with a continuum of inflammatory response between intercritical periods and acute attacks in chronic gout.

In some instances, the inflammatory response is initiated when microcrystals shed from microtophi adjacent to the joint space and enter the synovial fluid. In addition to their location, the size of the crystals may be a significant factor. New microcrystals that form and those that break off from larger crystals appear to be essential to the process. In certain instances, this observation may also explain why aggressive antihyperuricemic therapy may trigger a mobilization flare: it can cause larger crystals to dissolve and release microcrystals. Thus, prophylactic treatment with anti-inflammatory drugs has been recommended for 6 months or longer after the start of antihyperuricemic therapy, while urate levels are in flux.

Many biochemical mediators are involved in the inflammatory response. Monocytes play a large role, releasing proinflammatory cytokines and attracting neutrophils to the site, thus amplifying the response. Phagocytes resident within the synovium may be insufficient to trigger an immune response to microcrystals. However, the entry of new monocytes and neutrophils may shift the immune balance, leading to the gout flare.

Therapeutic Agents for Treatment of Gout

NSAIDs

NSAIDS are the usual first line treatment for gout with no significant difference between agents in effectiveness. Improvements are often seen within 4 hours. They however are not recommended in those with certain other health problems such as gastrointestinal bleeding, renal failure, or heart failure. While indomethacin is historically the most commonly used NSAID, due to concerns of side effects and no evidence of greater benefit, an alternative like ibuprofen may be preferred. For those at risk of gastric irritation from NSAIDs, an additional proton pump inhibitor may be given. NSAIDs include but are not limited to aminoarylcarboxylic acid derivatives such as enfenamic acid, etofenamate, flufenamic acid, isonixin, meclofenamic acid, mefenamic acid, niflumic acid, talniflumate, terofenamate, and tolfenamic acid; arylacetic acid derivatives such as aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac isoxepac, lonazolac, metiazinic acid, mofezolac, oxametacine, pirazolac, proglumetacin, sulindac, tiaramide, tolmetin, tropesin, and zomepirac; arylbutyric acid derivatives such as bumadizon, butibufen, fenbufen, xenbucin; arylcarboxylic acids such as clidanac, ketorolac, tinoridine; arylpropionic acid derivatives such as alminoprofen, benoxaprofin, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprofin, pirprofen, pranoprofen, protizinic acid, suprofen, tiaprofenic acid, ximoprofen, and zaltoprofen; pyrazoles such as difenamizole, and epirozole; pyrazolones such as apazone, benzpiperylon, feprazone, mofebutazone, morazone, oxyphenbutazone, phenylbutazone, pipebuzone, propyphenazone, prostaglandins, ramifenazone, suxibuzone, and thiazolinobutazone; salicylic acid derivatives such as acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphtyl salicylate, olsalazine, parsalmide, phenyl acetylsalicylate, phenyl salicylate, salacetamide, salicylamide o-acetic acid, salicylsulfuric acid, salsalate, sulfasalazine; thiazinecarboxamides such as ampiroxicam, droxicam, isoxicam, lomoxicam, piroxicam, and tenoxicam; cyclooxygenase-II inhibitors ("COX-II") such as Celebrex (Celecoxib), Vioxx, Relafen, Lodine, and Voltaren and others, such as epsilon-acetamidocaproic acid, s-adenosylmethionine, 3-amino-4-hydroxybutylic acid, amixetrine, bendazac, benzydamine, α-bisabolol, bucololome, difenpiramide, ditazol, emorfazone, fepradinol, guaiazulene, nabumetone, nimesulide, oxaceprol, paranyline, perisoxal, proquazone, tenidap and zilenton; sleep aids including but not limited to a benzodiazepine hypnotic, non-benzodiazepine hypnotic, antihistamine hypnotic, antidepressant hypnotic, herbal extract, barbiturate, peptide hypnotic, triazolam, brotizolam, loprazolam, lormetazepam, flunitrazepam, flurazepam, nitrazepam, quazepam, estazolam, temazepam, lorazepam, oxazepam, diazepam, halazepam, prazepam, alprazolam, chlordiazepoxide, clorazepate, an imidazopyridine or pyrazolopyrimidine hypnotic, zolpidem or zolpidem tartarate, zopiclone, eszopiclone, zaleplon, indiplone, diphenhydramine, doxylamine, phenyltoloxamine, pyrilamine, doxepin, amtriptyline, trimipramine, trazodon, nefazodone, buproprion, bupramityiptyline, an herbal extract such as valerian extract or amentoflavone, a hormone such as melatonin, or gabapeptin.

Steroids

Glucocorticoids have been found to be equally effective to NSAIDs and may be used if contraindications exist for NSAIDs. Intra-articular steroids have also been found to be effective however the risk of concurrent joint infection must be ruled out.

Colchicine

Colchicine is an alternative therapeutic agent for those unable to tolerate NSAIDs. Side effects (primarily gastrointestinal upset) associated with colchicine has decreased its usage. Gastrointestinal upset however depends on the dose and the risk is decreased by using smaller yet still effective doses. Colchicine may interact with other commonly prescribed drugs such as atorvastatin and erythromycin among others. When administered in the formulation marketed as COLCRYS (cholchicine, USP), the recommended dose for the prophylaxis of gout flares is 0.6 mg once or twice daily. For the treatment of gout flares the recommended dose is 1.2 mg at first indication of a flare followed by 0.6 mg one hour later.

Agents which have found use in the treatment of gout are P2X receptor inhibitors, reactive oxygen species inhibitors, toll like receptor antagonists, IL1 inhibitors—anakinra, rilonacept, TNF blockers—enbrel etc., glucocorticoids prednisone, prednisolone, triamcinolone, dexamethasone, inflammasome inhibitors, caspase inhibitors, NSAIDS—celecoxib, Ibuprofen, naproxen, fenbufen, fenoprofen, flurbiprofen, ketoprofen, tiaprofenic acid, azapropazone, diclofenac, diflunisal, etodolac, indomethacin (indometacin), ketorolac, mefenamic, meloxicam, nabumetone, phenylbutazone, piroxicam, sulindac, tenoxicam, tolfenamic acid, hydroxychloroquine (Plaquenil) or chloroquine (Aralen), leflunomide (Arava), methotrexate, sulfasalazine azulfidine, Abatacept (Orencia), Adalimumab (Humira), Anakinra (Kineret), Etanercept (Enbrel), Infliximab (Remicade), Rituximab (Rituxan).

URAT1

URAT1 is a urate transporter and urate-anion exchanger which regulates the level of urate in the blood. This protein is an integral membrane protein primarily found in kidney.

Inflammasome

The inflammasome is responsible for activation of inflammatory processes, and has been shown to induce cell pyroptosis, a process of programmed cell death distinct from apoptosis. The inflammasome is a multiprotein complex consisting of caspase 1, PYCARD, a NALP and sometimes caspase 5 or caspase 11. The exact composition of an inflammasome depends on the activator which initiates inflammasome assembly i.e., dsRNA will trigger one inflammasome composition whereas asbestos will assemble a different variant. The inflammasome promotes the maturation of inflammatory cytokines interleukin 1-β and interleukin 18.

Sodium 2-(5-bromo-4-(4-cyclopropylnaphthalen-1-yl)-4H-1,2,4-triazol-3-ylthio)acetate Some embodiments provided herein relate to methods for treating or preventing diseases, comprising administering an effective amount of sodium 2-(5-bromo-4-(4-cyclopropylnaphthalen-1-yl)-4H-1,2,4-triazol-3-ylthio)acetate.

Sodium 2-(5-bromo-4-(4-cyclopropylnaphthalen-1-yl)-4H-1,2,4-triazol-3-ylthio)acetate is known to decrease uric acid levels, (see for example U.S. publication 2009-0197825, U.S. patent application Ser. No. 12/553,844 and U.S. patent application Ser. No. 12/554,719). Details of clinical studies involving sodium 2-(5-bromo-4-(4-cyclopropylnaphthalen-1-yl)-4H-1,2,4-triazol-3-ylthio)acetate have been described in U.S. provisional patent application 61/252,530, U.S. provisional patent application 61/252,537 and U.S. provisional patent application 61/265,240.

Uric acid is the result of the oxidation of xanthine. Disorders of uric acid metabolism include, but are not limited to, polycythemia, myeloid metaplasia, gout, a recurrent gout attack, gouty arthritis, hyperuricaemia, hypertension, a cardiovascular disease, coronary heart disease, Lesch-Nyhan syndrome, Kelley-Seegmiller syndrome, kidney disease, kidney stones, kidney failure, joint inflammation, arthritis, urolithiasis, plumbism, hyperparathyroidism, psoriasis or sarcoidosis.

Definitions

The term "subject", as used herein in reference to individuals suffering from a disorder, and the like, encompasses mammals and non-mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. Examples of non-mammals include, but are not limited to, birds, fish and the like. In one embodiment of the methods and compositions provided herein, the mammal is a human.

The terms "effective amount", "therapeutically effective amount" or "pharmaceutically effective amount" as used herein, refer to an amount of at least one agent or compound being administered that is sufficient to treat or prevent the particular disease or condition. The result can be reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in a disease. An appropriate "effective" amount in any individual case may be determined using techniques, such as a dose escalation study.

Modulating URAT-1 Activity

Certain embodiments provided herein describe methods of modulating URAT-1 activity by contacting URAT-1 with an amount of sodium 2-(5-bromo-4-(4-cyclopropylnaphthalen-1-yl)-4H-1,2,4-triazol-3-ylthio)acetate, as described herein, sufficient to modulate the activity of URAT-1. In some embodiments, contacting URAT-1 with a sufficient amount of sodium 2-(5-bromo-4-(4-cyclopropylnaphthalen-1-yl)-4H-1,2,4-triazol-3-ylthio)acetate inhibits URAT-1 activity. In other embodiments, contacting URAT-1 with a sufficient amount of sodium 2-(5-bromo-4-(4-cyclopropylnaphthalen-1-yl)-4H-1,2,4-triazol-3-ylthio)acetate activates URAT-1 activity.

Also provided herein, in some embodiments, is a method of inhibiting URAT-1 activity by contacting URAT-1 with an amount of sodium 2-(5-bromo-4-(4-cyclopropylnaphthalen-1-yl)-4H-1,2,4-triazol-3-ylthio)acetate, as described herein, sufficient to inhibit the activity of URAT-1. In some embodiments, described herein is a method of inhibiting URAT-1 activity in a solution by contacting said solution with an amount of sodium 2-(5-bromo-4-(4-cyclopropylnaphthalen-1-yl)-4H-1,2,4-triazol-3-ylthio)acetate, as described herein sufficient to inhibit the activity of URAT-1 in said solution. In some embodiments, described herein is a method of inhibiting URAT-1 activity in a cell by contacting said cell with an amount of sodium 2-(5-bromo-4-(4-cyclopropylnaphthalen-1-yl)-4H-1,2,4-triazol-3-ylthio)acetate, as described herein, sufficient to inhibit the activity of URAT-1 in said cell. In some embodiments, described herein is a method of inhibiting URAT-1 activity in a tissue by contacting said tissue with an amount of sodium 2-(5-bromo-4-(4-cyclopropylnaphthalen-1-yl)-4H-1,2,4-triazol-3-ylthio)acetate, as described herein, sufficient to inhibit the activity of URAT-1 in said tissue. In some embodiments, described herein is a method of inhibiting URAT-1 activity in blood by contacting the blood with an amount of sodium 2-(5-bromo-4-(4-cyclopropylnaphthalen-1-yl)-4H-1,2,4-triazol-3-ylthio)acetate, as described herein, sufficient to inhibit the activity of URAT-1 in blood. In other embodiments, described herein is a method of inhibiting URAT-1 activity in plasma by contacting the plasma with an amount of sodium 2-(5-bromo-4-(4-cyclopropylnaphthalen-1-yl)-4H-1,2,4-triazol-3-ylthio)acetate, as described herein, sufficient to inhibit the activity of URAT-1 in plasma. In some embodiments, described herein is a method of inhibiting URAT-1 activity in an animal by contacting said animal with an amount of sodium 2-(5-bromo-4-(4-cyclopropylnaphthalen-1-yl)-4H-1,2,4-triazol-3-ylthio)acetate, as described herein sufficient to inhibit the activity of URAT-1 in said animal. In some embodiments, the invention provides methods of inhibiting URAT-1 activity in a mammal by contacting said mammal with an amount of sodium 2-(5-bromo-4-(4-cyclopropylnaphthalen-1-yl)-4H-1,2,4-triazol-3-ylthio)acetate, as described herein sufficient to inhibit the activity of URAT-1 in said mammal. In some embodiments, described herein is a method of inhibiting URAT-1 activity in a human by contacting said human with an amount of sodium 2-(5-bromo-4-(4-cyclopropylnaphthalen-1-yl)-4H-1,2,4-triazol-3-ylthio)acetate, as described herein, sufficient to inhibit the activity of URAT-1 in said human.

Pharmaceutical Compositions

Described herein are pharmaceutical compositions comprising an effective amount of sodium 2-(5-bromo-4-(4-cyclopropylnaphthalen-1-yl)-4H-1,2,4-triazol-3-ylthio)acetate, as described herein. In some embodiments, the pharmaceutical compositions comprise an effective amount of sodium 2-(5-bromo-4-(4-cyclopropylnaphthalen-1-yl)-4H-1,2,4-triazol-3-ylthio)acetate, as described herein, and at least one pharmaceutically acceptable carrier. In some embodiments, the pharmaceutical compositions are for the treatment of disorders. In certain embodiments, the pharmaceutical compositions are for the treatment of disorders in a mammal. In certain specific embodiments, the pharmaceutical compositions are for the treatment of disorders in a human. In some embodiments, the pharmaceutical compositions are for the treatment or prophylaxis of disorders of uric acid metabolism. In some embodiments, the pharmaceutical compositions are for the treatment or prophylaxis of hyperuricemia. In other embodiments, the pharmaceutical compositions are for the treatment or prophylaxis of gout.

Modes of Administration, Formulations and Dosage Forms

Described herein are pharmaceutical compositions comprising sodium 2-(5-bromo-4-(4-cyclopropylnaphthalen-1-yl)-4H-1,2,4-triazol-3-ylthio)acetate, as described herein. In certain embodiments, the compound, compound forms and compositions described herein are administered either alone or in combination with pharmaceutically acceptable carriers, excipients or diluents, in a pharmaceutical composition, according to standard pharmaceutical practice. In some embodiments, administration is effected by any method that enables delivery of the compounds to the site of action. These methods include, though are not limited to, delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route depend upon for example the condition and disorder of the recipient. Those of skill in the art will be familiar with administration techniques that can be employed with the compounds and methods of the invention. By way of example only, the compounds, compound forms and compositions described herein can be administered locally to the area in need of treatment, by for example, local infusion during surgery, topical application such as creams or ointments, injection, catheter, or implant, said implant made for example, out of a porous, non-porous, or gelatinous material, including membranes, such as sialastic membranes, or fibers. In some embodiments, administration is by direct injection at the site of a diseased tissue or organ.

In some embodiments, the pharmaceutical compositions described herein is in a form suitable for oral administration (e.g., as a tablet, capsule, pill, powder, sustained release formulations, solution, suspension), for parenteral injection (e.g., as a sterile solution, suspension or emulsion), for topical administration (e.g., as an ointment or cream), or for rectal administration (e.g., as a suppository). In certain embodiments, the pharmaceutical composition is in unit dosage forms suitable for single administration of precise dosages. In further or additional embodiments, the pharmaceutical composition includes a conventional pharmaceutical carrier or excipient and a compound according to the invention as an active ingredient. In still further or additional embodiments, the pharmaceutical composition may include other medicinal or pharmaceutical agents, carriers, adjuvants, etc.

In some embodiments, the formulation is presented in unit dosage form and is prepared by any of the methods well known in the art of pharmacy. All methods include the step of bringing into association a compound or compound form of the subject invention or a pharmaceutically acceptable salt, ester, prodrug or solvate thereof ("active ingredient") with the carrier which constitutes one or more accessory ingredients. In general, the formulations are prepared by uniformly and intimately bringing into association the active ingredient with liquid carriers or finely divided solid carriers or both and then, if necessary, shaping the product into the desired formulation.

Doses

The amount of pharmaceutical compositions administered will firstly be dependent on the mammal being treated. In the instances where pharmaceutical compositions are administered to a human subject, the daily dosage will normally be determined by the prescribing physician with the dosage generally varying according to the age, sex, diet, weight, general health and response of the individual patient, the severity of the patient's symptoms, the precise indication or condition being treated, the severity of the indication or condition being treated, time of administration, route of administration, the disposition of the composition, rate of excretion, drug combination, and the discretion of the prescribing physician. In certain embodiments, the route of administration varies depending on the condition and its severity. In some embodiments, the pharmaceutical composition is in unit dosage form. In such form, the preparation is subdivided into unit doses containing appropriate quantities of the active component (e.g., an effective amount to achieve the desired purpose). In some embodiments, the total daily dosage is divided and administered in portions during the day if desired. The amount and frequency of administration will be regulated according to the judgment of the attending clinician (physician) considering such factors as described above. In certain embodiments, the amount of pharmaceutical composition to be administered will vary widely. When referring to a dosage amount, the quantity stated is of the active pharmaceutical ingredient. In some embodiments, administration occurs in an amount of between about 0.001 mg/kg of body weight to about 100 mg/kg of body weight per day (administered in single or divided doses), or at least about 0.1 mg/kg of body weight per day. In certain embodiments, a particular therapeutic dosage includes, e.g., from about 0.01 mg to about 7000 mg of compound, or, e.g., from about 0.05 mg to about 2500 mg. In further or additional embodiments, the quantity of active compound in a unit dose of preparation is varied or adjusted from about 0.1 mg to 1000 mg, from about 1 mg to 300 mg, or 10 mg to 200 mg, according to the particular application. In some instances, dosage levels below the lower limit of the aforesaid range are more than adequate, while in other cases still larger doses are employed without causing any harmful side effect, e.g. by dividing such larger doses into several small doses for administration throughout the day. In some embodiments, combinational applications in which the compound is not the sole therapy, allows for the administration of lesser amounts of compound and still have therapeutic or prophylactic effect.

In specific embodiments, an effective amount of an agent described herein is a therapeutic amount effective to reduce sUA, treat gout, or treat any disorder described herein. In some embodiments, an effective amount of a compound of formula I is greater than 50 mg, greater than 100 mg, greater than 150 mg, greater than 200 mg, greater than 250 mg, less than 1000 mg, less than 900 mg, less than 800 mg, less than 750 mg, less than 600 mg, less than 550 mg, less than 500 mg, less than 400 mg, less than 300 mg, less than 200 mg, less than 150 mg, less than 100 mg, about 10 mg to about 2000 mg, about 50 mg to about 1500 mg, about 50 mg to about 1000 mg, about 200 mg to about 1000 mg, about 200 mg to about 800 mg, about 300 mg to about 700 mg, about 300 mg to about 900 mg, about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1100 mg, about 1200 mg, about 1300 mg, about 1400 mg, about 1500 mg, or any other suitable dose. In certain embodiments, an effective amount administered according to any method described herein, or present in any composition described herein, comprises one, two, three, four, five, six, or more dosage forms. For example, in certain specific embodiments, an effective amount may comprise 1200 mg and may include a composition comprising or the administration of two 600 mg dosage forms (e.g., pills).

In certain embodiments, an effective amount of a xanthine oxidase (XO) inhibitor is any suitable amount. In specific embodiments, the xanthine oxidase (XO) inhibitor is allopurinol and the effective amount is about 50 mg to about 1000 mg, about 200 mg to about 500 mg, about 100 mg to about 300 mg, greater than about 50 mg, greater than about 100 mg, greater than about 150 mg, greater than about 200 mg, greater than about 250 mg, greater than about 300 mg, greater than about 350 mg, greater than about 400 mg, greater than about 450 mg, greater than about 500 mg, less than about 1000 mg, less than about 750 mg, less than about 600 mg, less than about 550 mg, less than about 500 mg, less than about 450 mg, less than about 400 mg, less than about 350 mg, less than about 300 mg, less than about 250 mg, less than about 200 mg, less than about 150 mg, less than about 100 mg, about 50 mg, about 75 mg, about 100 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 550 mg, about 600 mg, about 650 mg, about 700 mg, about 750 mg, about 800 mg, or any other suitable amount.

In other specific embodiments, the xanthine oxidase (XO) inhibitor is febuxostat, and the effective amount is about 10 mg to about 300 mg, about 30 mg to about 150 mg, about 40 mg to about 80 mg, greater than about 50 mg, greater than about 100 mg, greater than about 150 mg, greater than about 200 mg, greater than about 250 mg, greater than about 300 mg, greater than about 350 mg, greater than about 400 mg, greater than about 450 mg, greater than about 500 mg, less than about 1000 mg, less than about 750 mg, less than about 600 mg, less than about 550 mg, less than about 500 mg, less than about 450 mg, less than about 400 mg, less than about 350 mg, less than about 300 mg, less than about 250 mg, less than about 200 mg, less than about 150 mg, less than about 100 mg, about 40 mg, about 45 mg, about 50 mg, about 75 mg, about 80 mg, about 100 mg, about 120 mg, about 125 mg, about 150 mg, about 175 mg, about 200 mg, about 225 mg, about 250 mg, about 275 mg, about 300 mg, about 325 mg, about 350 mg, about 375 mg, about 400 mg, about 425 mg, about 450 mg, about 475 mg, about 500 mg, about 550 mg, about 600 mg, about 650 mg, about 700 mg, about 750 mg, about 800 mg, or any other suitable amount.

Combination Therapies

In some embodiments, the compounds and compound forms described herein are administered as a sole therapy or in combination with another therapy or therapies.

By way of example only, if one of the side effects experienced by a patient upon receiving a compound or compound form as described herein is hypertension, then it may be appropriate to administer an anti-hypertensive agent in combination with the compound. Or, by way of example only, the therapeutic effectiveness of a compound or compound form as described herein may be enhanced by administration of an adjuvant (i.e., by itself the adjuvant may only have minimal therapeutic benefit, but in combination with another therapeutic agent, the overall therapeutic benefit to the patient is enhanced). Or, by way of example only, the benefit experienced by a patient may be increased by administering a compound or compound form as described herein with another therapeutic agent (which also includes a therapeutic regimen) that also has therapeutic benefit. Regardless of the disease, disorder or condition being treated, the overall benefit experienced by the patient may simply be additive of the two therapeutic agents or the patient may experience a synergistic benefit.

In the instances where the compounds or compound forms as described herein are administered with other therapeutic agents, they need not be administered in the same pharmaceutical composition as other therapeutic agents, and may, because of different physical and chemical characteristics, be administered by a different route. For example, the compound or compound form as described herein may be administered orally to generate and maintain good blood levels thereof, while the other therapeutic agent may be administered intravenously. The determination of the mode of administration and the advisability of administration, where possible, in the same pharmaceutical composition, is well within the knowledge of the skilled clinician. The initial administration can be made according to established protocols, and then, based upon the observed effects, the dosage, modes of administration and times of administration can be modified by the skilled clinician.

The compounds, compound forms and compositions described herein (and where appropriate other chemotherapeutic agent) may be administered concurrently (e.g., simultaneously, essentially simultaneously or within the same treatment protocol) sequentially or separately, depending upon the nature of the disease, the condition of the patient, and the actual choice of other chemotherapeutic agent to be administered. For combinational applications and uses, the compounds, compound forms and compositions described herein and the chemotherapeutic agent need not be administered simultaneously or essentially simultaneously. Thus, the compounds, compound forms and compositions as described herein may be administered first followed by the administration of the chemotherapeutic agent; or the chemotherapeutic agent may be administered first followed by the administration of the compounds, compound forms and compositions as described herein. This alternate administration may be repeated during a single treatment protocol. The determination of the order of administration, and the number of repetitions of administration of each therapeutic agent during a treatment protocol, is well within the knowledge of the skilled physician after evaluation of the disease being treated and the condition of the patient. For example, the chemotherapeutic agent may be administered first, especially if it is a cytotoxic agent, and then the treatment continued with the administration of the compounds, compound forms and compositions as described herein followed, where determined advantageous, by the administration of the chemotherapeutic agent, and so on until the treatment protocol is complete. Thus, in accordance with experience and knowledge, the practicing physician can modify each administration protocol for treatment according to the individual patient's needs, as the treatment proceeds. The attending clinician, in judging whether treatment is effective at the dosage administered, will consider the general well-being of the patient as well as more definite signs such as relief of disease-related symptoms. Relief of disease-related symptoms such as pain, and improvement in overall condition can also be used to help judge effectiveness of treatment.

Specific, non-limiting examples of possible combination therapies include use of the compounds and compositions described herein with Febuxostat, Allopurinol, Probenacid, Sulfinpyrazone, Losartan, Fenofibrate, Benzbromarone or PNP-inhibitors (such as, but not limited to Forodesine, BCX-1777 or BCX-4208). This list should not be construed to be closed, but should instead serve as an illustrative example common to the relevant therapeutic area at present. Moreover, combination regimens may include a variety of routes of administration, including but not limited to oral, intravenous, intraocular, subcutaneous, dermal, and inhaled topical.

In specific embodiments, a compound of formula I is administered in combination with a xanthine oxidase (XO) inhibitor. In other specific embodiments, a therapy described herein comprises administering to an individual in need thereof an effective amount of a compound of formula I and an effective amount of an XO inhibitor. In more specific embodiments, the XO inhibitor is allopurinol or febuxostat. Moreover, certain embodiments provided for herein comprise an effective amount of a compound of formula I and an effective amount of an XO inhibitor. In certain embodiments, an effective amount of a compound of formula I and/or an XO inhibitor are as described herein. In some embodiments, an effective amount of a compound of formula I and/or an XO inhibitor are lower when in combination, or administered in combination, than when alone, or administered alone. In some embodiments, therapies described herein begin with the administration of an XO inhibitor alone (e.g., for a week), followed by a first dose of a compound of formula I (e.g., in combination with the XO inhibitor) for a period of time (e.g., for a week), followed by a second dose of a compound of formula I (e.g., in combination with the XO inhibitor) for a period of time (e.g., for a week), etc. In various embodiments, the first dose is greater than the second dose; in other embodiments, the first dose is less than the second dose. Thus, the dose of the compound of formula I is optionally increased in order to titrate sUA to a desired level.

In some embodiments, the present invention describes positive, preliminary, top-line results from its Phase 2b study of a compound of formula I in combination with the current standard of care for the treatment of gout, allopurinol. Allopurinol currently accounts for greater than 90% of the unit sales of chronic gout prescription medications; however, in controlled trials, only 30-40% of gout patients respond adequately to allopurinol as defined by the achievement of a serum uric acid (sUA) level of less than 6 mg/dL, the medically recommended target. In some embodiments of the Phase 2b study, the primary and key secondary endpoints were achieved, with highly statistically significant reductions in sUA and up to 89% of patients taking a combination of 600 mg of a compound of formula I, and allopurinol reaching target sUA. In some embodiments, a compound of formula I, a lead product candidate for the chronic treatment of gout, is an orally administered compound that inhibits the URAT1 transporter, a biological mechanism that is complementary to the mechanism of allopurinol and that of the most recently approved oral drug for gout, febuxostat (Uloric®).

Provided herein in certain embodiments is a 28-day, randomized, double-blind, placebo-controlled, study was conducted in 208 gout patients with elevated uric acid levels (sUA greater than or equal to 6 mg/dL) despite being on a stable dose of allopurinol. In some embodiments, patients remained on a stable dose of allopurinol and also received once daily doses of 200 mg a compound of formula I, 400 mg of a compound of formula I, 600 mg of a compound of formula I, or placebo. In some embodiments, a stable dose of allopurinol is greater than 300 mg/day, less than 300 mg/day, about 50 mg/day, about 75 mg/day, about 100 mg/day, about 125 mg/day, about 150 mg/day, about 175 mg/day, about 200 mg/day, about 225 mg/day, about 250 mg/day, about 275 mg/day, about 300 mg/day, about 325 mg/day, about 350 mg/day, about 375 mg/day, about 400 mg/day, about 425 mg/day, about 450 mg/day, about 475 mg/day, about 500 mg/day, or any other suitable amount. In some embodiments, for patients randomized to receive 400 mg a compound of formula I and 600 mg of a compound of formula I, a daily dose of compound of formula I was escalated weekly in increments of 200 mg/day. In certain embodiments, a primary endpoint of the study was the percent reduction in sUA after 4 weeks of treatment with the combination compared to allopurinol alone. In some certain embodiments, a key secondary efficacy endpoint was the proportion of patients who achieved a response, defined as a reduction of sUA below the clinically relevant target of <6 mg/dL, after 4 weeks of combined compound of formula I and allopurinol treatment, compared to allopurinol and placebo.

In certain embodiments, reductions in sUA and response rates increased in a dose-related manner when a compound of formula I was combined with allopurinol and were highly clinically and statistically significant at all dose levels when compared to allopurinol alone. In certain specific embodiments, at the highest dose tested of 600 mg, there was a 30% mean reduction in sUA levels after 4 weeks, compared to a 3% mean increase on placebo (p<0.0001). In some embodiments, provided herein is a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject, wherein said method provides a mean change in serum urate levels of greater than 8%, greater than 10%, greater than 12%, greater than 15%, greater than 17%, greater than 20%, greater than 23%, greater than 25%, greater than 28%, greater than 30%, greater than 33%, greater than 35%, greater than 40%, greater than 50%, greater than 60%, greater than 70%, greater than 80%, greater than 90%, or greater than 95%. In a certain embodiment, the method provides a mean change in serum urate levels of greater than 10%.

In some embodiments, a response rate of 79% for the 600 mg dose (p<0.0001) using the more rigorous "intent-to-treat" (ITT) analysis resulted, which considers all patients without efficacy results at Week 4 as non-responders, including those who discontinue for any reason. In other embodiments, a "last observation carried forward" (LOCF) analysis was used, which was the analysis method used for the approval of Uloric®, the response rate for the 600 mg dose group was 89% (p<0.0001). In some embodiments, provided herein is a method of treating gout comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to a subject, wherein said method provides a response rate (e.g., ITT analysis) of greater than 35%, greater than 40%, greater than 45%, greater than 50%, greater than 55%, greater than 60%, greater than 65%, greater than 70%, greater than 75%, greater than 80%, greater than 85%, greater than 90%, or greater than 95%. In certain embodiments, the method provides a response rate (e.g., ITT analysis) of greater than 60%.

Preliminary, Top-Line Efficacy Results of Phase 2b Combination Therapy Study of Compound of Formula I in Allopurinol-Refractory Patients with Gout

|  | Treatment Groups | | | |
| --- | --- | --- | --- | --- |
|  | Formula I 600 mg qd + allopurinol | Formula I 400 mg qd + allopurinol | Formula I 200 mg qd + allopurinol | Placebo qd + allopurinol |
| Response Rate (ITT Analysis) | 79% (n = 48) $p < 0.0001$ | 74% (n = 42) $p < 0.0001$ | 63% (n = 46) $p < 0.0001$ | 25% (n = 72) |
| Response Rate (LOCF Analysis) | 89% (n = 45) $p < 0.0001$ | 76% (n = 42) $p < 0.0001$ | 71% (n = 45) $p < 0.0001$ | 29% (n = 70) |
| Mean Change in Serum Urate at Week 4 vs. Baseline on Allopurinol Alone | −30% $p < 0.0001$ | −22% $p < 0.0001$ | −16% $p < 0.0001$ | +3% | p-values versus allopurinol + placebo

In certain embodiments, the combination of a compound of formula I and allopurinol was well tolerated in this study. In certain specific embodiments, the only serious adverse event in the study, a fatal myocardial infarction, occurred on allopurinol alone. In some embodiments, no serious adverse events or deaths occurred while patients were on a compound of formula I. In certain embodiments, adverse events were infrequent, not dose related and comparable between the groups receiving a compound of formula I and placebo. In specific embodiments, five patients discontinued treatment due to an adverse event; three occurred on allopurinol alone and two occurred on the combination of allopurinol and a compound of formula I. In some embodiments, provided herein is a method of treating gout comprising co-administration of a compound of formula I, or a pharmaceutically acceptable salt thereof, and allopurinol to a subject, wherein said method results in a treatment-related adverse event in less than 1%, less than 2%, less than 4%, less than 5%, less than 6%, less than 7%, less than 8%, less than 9%, less than 10%, less than 11%, less than 12%, less than 13%, or less than 15% of the subjects.

Preliminary Safety Results of Phase 2b Combination Therapy Study of a Compound of Formula I in Allopurinol-Refractory Gout Patients Percent of Patients with Treatment-Related Adverse Events Occurring in More Than One Patient

|  | Treatment Groups | | | | |
| --- | --- | --- | --- | --- | --- |
|  | Formula I 600 mg qd + allopurinol | Formula I 400 mg qd + allopurinol | Formula I 200 mg qd + allopurinol | Formula I All Doses + allopurinol | Pooled Placebo + allopurinol |
| Number of patients | 48 | 42 | 46 | 136 | 72 |
| Any Adverse Event | 10.4% | 9.5% | 2.2% | 7.4% | 13.9% |
| Diarrhea | 0% | 2.4% | 0% | 0.7% | 2.8% |
| Dyspepsia | 2.1% | 0% | 0% | 0.7% | 1.4% |
| Dizziness | 0% | 0% | 2.2% | 0.7% | 2.8% |
| Lipase Increased | 0% | 2.4% | 0% | 0.7% | 1.4% |
| Hematuria | 0% | 2.4% | 0% | 0.7% | 2.8% |

In some embodiments, the compound of formula I is administered alone or in combination with other agents to an individual who is not adequately treated with currently available products.

In some embodiments, a compound of formula I is an oral, once-daily inhibitor of URAT1, which is a transporter in the kidney that regulates uric acid excretion from the body, In another embodiment, the compound of formula I is used for the treatment of hyperuricemia and gout. In certain embodiments, approximately 90% of gout patients are considered to be under-excretors of uric acid, and recent studies have shown that defects in renal transporters have been genetically linked to gout. In further or additional embodiments, increasing renal excretion of uric acid by moderating URAT1 transporter activity may provide the most physiologically appropriate treatment for gout. In yet further or additional embodiments, because increasing the excretion of serum uric acid is additive to the effects of drugs that decrease the production of uric acid, such as allopurinol and febuxostat, a compound of formula I in combination with such drugs has the potential to treat the significant portion of the gout population that is not adequately treated with existing therapies.

In certain embodiments, a compound of formula I is in Phase 2 development as a single agent and in combination with the approved xanthine oxidase inhibitor, allopurinol. In some embodiments, over 500 people have received a compound of formula I in Phase 1 and 2 clinical trials.

Also provided herein in certain embodiments is an open-label, clinical pharmacology study including 2 cohorts of gout patients with sUA greater than 8 mg/dL on no urate-lowering therapy. In some embodiments, patients received colchicine beginning one week prior to baseline and continuing for 5 weeks for flare prophylaxis. In other embodiments, the first cohort of patients in the study consisted of gout patients with a median baseline sUA of 9.2 mg/dL who were administered 40 mg febuxostat for the first week, 40 mg febuxostat in combination with 400 mg of a compound of formula I for the second week, and then 40 mg febuxostat in combination with 600 mg of a compound of formula I for the third week. In some embodiments, this sequence was repeated with 80 mg febuxostat in a second cohort of patients who had a median baseline sUA of 10.4 mg/dL. In some embodiments, less than 40 mg, greater than 40 mg, less than 80 mg, greater than 80 mg, or any suitable amount of febuxostat was administered. In certain embodiments, 100% of patients receiving the combination of a compound of formula I and febuxostat achieved serum urate (or "sUA") levels below the clinically important target of 6 mg/dL, compared to 67 percent and 56 percent for 40 mg and 80 mg, respectively, of febuxostat alone. In some embodiments, about 100%, about 99%, about 98%, about 97%, about 96%, about 95%, about 90%, about 85%, about 80%, about 75%, about 50%, greater than about 75%, greater than about 80%, greater than about 90%, greater than about 95%, or greater than about 98% of patients receiving the combination of a compound of formula I and febuxostat achieved serum urate (or "sUA") levels below the clinically important target of 6 mg/dL. In some embodiments, at the highest combination doses tested of a compound of formula I, about 100%, about 99%, about 98%, about 97%, about 96%, about 95%, about 90%, about 85%, about 80%, about 75%, about 50%, greater than about 75%, greater than about 80%, greater than about 90%, greater than about 95%, or greater than about 98% of patients also reached sUA levels below 4 mg/dL, with 58 percent achieving levels below 3 mg/dL.

In some embodiments, no patient achieved these reduced sUA levels on either dose of febuxostat alone. In certain embodiments, the combination of a compound of Formula I and febuxostat was synergistic, with the addition of 600 mg of a compound of Formula I producing additional 39 and 51 percent reductions compared to 40 mg and 80 mg febuxostat alone, respectively. In certain specific embodiments, patients receiving the highest combination doses in cohorts one and two achieved intraday median sUA levels of 2.4 mg/dL and 2.0 mg/dL, respectively. In certain embodiments, these levels of sUA reduction suggest the combination of a compound of Formula I and febuxostat may be particularly useful in patients who have accumulated large deposits of uric acid, or tophi. In some embodiments, the substantial reduction of sUA in patients, coupled with increased excretion of uric acid associated with a compound of Formula I URAT1 mechanism, may lead to improved resolution of these tophi.

In some embodiments, no clinically relevant drug interactions were observed between a compound of Formula I and febuxostat. In some embodiments, the combination of a compound of Formula I and febuxostat does not increase risk for kidney stones. In some embodiments, the combination of a compound of Formula I and febuxostat does not increase risk for kidney stones based on the analysis of 24 h undissociated urine urate levels. In some embodiments, the combination of a compound of Formula I and febuxostat provides mean (SE) undissociated urine urate levels below 10 mg/dL, 9, mg/dL, 8 mg/dL, 7 mg/dL, 6 mg/dL, 5.5 mg/dL, 5 mg/dL, 4.5 mg/dL, 4 mg/dL, 3.5 mg/dL, 3 mg/dL, 2.5 mg/dL, 2 mg/dL, or 1.5 mg/dL. In certain embodiments, the combination of a compound of Formula I and febuxostat provides mean (SE) undissociated urine urate levels of about 1.6 mL In some embodiments, the combination of a compound of Formula I and febuxostat increases the urine pH increases in gout patients. In other embodiments, the urine pH remains unchanged in gout patients when treated with a compound of Formula I and febuxostat. In certain embodiments, the mean (SE) 24 h urine pH is about 6.3, 6.2, 6.1, 6.0, 5.9, 5.8, 5.7, 5.6, 5.5, or 5.4. In certain embodiments, the mean (SE) 24 h urine pH is greater than 5.5, greater than 5.6, greater than 5.7, greater than 5.8, or greater than 5.9.

In some embodiments, the combination of a compound of Formula I and febuxostat increases the steady state plasma of febuxostat exposure compared to febuxostat alone. In certain embodiments, the pharmacokinetics of febuxostat is altered by co-administration with a compound of formula I. In further or additional embodiments, co-administration of a compound of Formula I and febuxostat increases febuxostat exposure by about 50%, 45%, 38%, 35%, 33%, 30%, 28%, 25%, 23%, 20%, 15%, 10%, or 5% compared to administration of febuxostat alone. In certain specific embodiments, co-administration of a compound of Formula I and febuxostat increases febuxostat exposure by about 30% compared to administration of febuxostat alone. In some embodiments, the pharmacokinetics of a compound of Formula I is not altered by co-administration with febuxostat. In other embodiments, the pharmacokinetics of a compound of Formula I is altered by co-administration with febuxostat.

In some embodiments, the combination of a compound of Formula I and febuxostat was well tolerated, with no serious adverse events or discontinuations due to adverse events. In some embodiments, provided herein is a method of treating gout comprising co-administration of a compound of formula I, or a pharmaceutically acceptable salt thereof, and febuxostat to a subject, wherein said method results in a treatment-related adverse event in less than 1%, less than 2%, less than 4%, less than 5%, less than 6%, less than 7%, less than 8%, less than 9%, less than 10%, less than 11%, less than 12%, less than 13%, or less than 15%, or less than 17%, or less than 20%, or less than 22%, or less than 25%, or less than 27%, or less than 30%, or less than 33%, or less than 35% of the subjects. In some embodiments, the adverse events include but are not limited to dyspepsia, gout flares, headache, nausea, dizziness, diarrhea, lipase increased, or hematuria. In certain specific embodiments, the adverse events are dyspepsia, gout flares and headaches.

Diseases

Described herein are methods of treating a disease or disorder in an individual suffering from said disease or disorder comprising administering to said individual an effective amount of sodium 2-(5-bromo-4-(4-cyclopropylnaphthalen-1-yl)-4H-1,2,4-triazol-3-ylthio)acetate.

The invention extends to the use of the compounds and compound forms described herein in the manufacture of a medicament for treating a disease or disorder.

In some embodiments, the disease or disorder is hyperuricemia. In certain instances, hyperuricemia is characterized by higher than normal blood levels of uric acid, sustained over long periods of time. In certain instances, increased blood urate levels may be due to enhanced uric acid production (~10-20%) and/or reduced renal excretion (~80-90%) of uric acid. In certain instances, causes of hyperuricemia may include obesity/weight gain, excessive alcohol use, excessive dietary purine intake (foods such as shellfish, fish roe, scallops, peas lentils, beans and red meat, particularly offal—brains, kidneys, tripe, liver), certain medications, including low-dose aspirin, diuretics, niacin, cyclosporine, pyrazinamide, ethambutol, some high blood pressure drugs and some cancer chemotherapeutics, immunosuppressive and cytotoxic agents, specific disease states, particularly those associated with a high cell turnover rate (such as malignancy, leukemia, lymphoma or psoriasis), and also including high blood pressure, hemoglobin diseases, hemolytic anemia, sickle cell anemia, various nephropathies, myeloproliferative and lymphoproliferative diseases, hyperparathyroidism, renal disease, conditions associated with insulin resistance and diabetes mellitus, and in transplant recipients, and possibly heart disease, inherited enzyme defects, abnormal kidney function (e.g. increased ATP turn over, reduced glomerular urate filtration) and exposure to lead (plumbism or "saturnine gout").

In certain instances, hyperuricemia may be asymptomatic, though is associated with the following conditions: gout, gouty arthritis, uric acid stones in the urinary tract (urolithiasis), deposits of uric acid in the soft tissue (tophi), deposits of uric acid in the kidneys (uric acid nephropathy), and impaired kidney function, possibly leading to chronic and acute renal failure.

In further or additional embodiments, the disease or disorder is gout, which is a condition that results from uric acid crystals depositing in tissues of the body. It is often related to an inherited abnormality in the body's ability to process uric acid, but may also be exacerbated by a diet high in purines. Defective uric acid processing may lead to elevated levels of uric acid in the blood causing recurring attacks of joint inflammation (arthritis), uric acid deposits in and around the joints, tophaceous gout, formation of tophi, decreased kidney function, and kidney stones. Approximately 3-5 million people in the United States suffer from attacks of gout with attacks 6 to 9 times more common in men than in women (see Sanders and Wortmann, "Harrison's Principles of Internal Medicine", 16th Edition; 2005; Food and Drug Administration (FDA) Advisory Committee Meeting, Terkeltaub presentation, June 2004; Terkeltaub, "Gout", *N Engl J Med.,* 349, 1647-55, 2003). In certain instances, gout is one of the most common forms of arthritis, accounting for approximately 5% of all arthritis cases. In certain instances, kidney failure and urolithiasis occur in 10-18% of individuals with gout and are common sources of morbidity and mortality from the disease.

Gout is associated with hyperuricemia. In certain instances, individuals suffering from gout excrete approximately 40% less uric acid than nongouty individuals for any given plasma urate concentration. In certain instances, urate levels increase until the saturation point is reached. In certain instances, precipitation of urate crystals occurs when the saturation point is reached. In certain instances, these hardened, crystallized deposits (tophi) form in the joints and skin, causing joint inflammation (arthritis). In certain instances, deposits are be made in the joint fluid (synovial fluid) and/or joint lining (synovial lining). Common areas for these deposits are the large toe, feet, ankles and hands (less common areas include the ears and eyes). In certain instances, the skin around an affected joint becomes red and shiny with the affected area being tender and painful to touch. In certain instances, gout attacks increase in frequency. In certain instances, untreated acute gout attacks lead to permanent joint damage and disability. In certain instances, tissue deposition of urate leads to: acute inflammatory arthritis, chronic arthritis, deposition of urate crystals in renal parenchyma and urolithiasis. In certain instances, the incidence of gouty arthritis increases 5 fold in individuals with serum urate levels of 7 to 8.9 mg/dL and up to 50 fold in individuals with levels >9 mg/dL (530 μmol/L). In certain instances, individuals with gout develop renal insufficiency and end stage renal disease (i.e., "gouty nephropathy"). In certain instances, gouty nephropathy is characterized by a chronic interstitial nephropathy, which is promoted by medullary deposition of monosodium urate.

In certain instances, gout includes painful attacks of acute, monarticular, inflammatory arthritis, deposition of urate crystals in joints, deposition of urate crystals in renal parenchyma, urolithiasis (formation of calculus in the urinary tract), and nephrolithiasis (formation of kidney stones). In certain instances, secondary gout occurs in individuals with cancer, particularly leukemia, and those with other blood diseases (e.g. polycythemia, myeloid metaplasia, etc).

In certain instances, attacks of gout develop very quickly, frequently the first attack occurring at night. In certain instances, symptoms include sudden, severe joint pain and extreme tenderness in the joint area, joint swelling and shiny red or purple skin around the joint. In certain instances, the attacks are infrequent lasting 5-10 days, with no symptoms between episodes. In certain instances, attacks become more frequent and last longer, especially if the disease is not controlled. In certain instances, episodes damage the affected joint(s) resulting in stiffness, swelling, limited motion and/or persistent mild to moderate pain.

Plumbism or "saturnine gout," is a lead-induced hyperuricemia that results from lead inhibition of tubular urate transport causing decreased renal excretion of uric acid. In certain instances, more than 50% of individuals suffering from lead nephropathy suffer from gout. In certain instances, acute attacks of saturnine gout occur in the knee more frequently than the big toe. In certain instances, renal disease is more frequent and more severe in saturnine gout than in primary gout. In certain instances, treatment consists of excluding the individual from further exposure to lead, the use of chelating agents to remove lead, and control of acute gouty arthritis and hyperuricaemia. In certain instances, saturnine gout is characterized by less frequent attacks than primary gout. In certain instances, lead-associated gout occurs in pre-menopausal women, an uncommon occurrence in non lead-associated gout.

In certain instances, Lesch-Nyhan syndrome (LNS or Nyhan's syndrome) affects about one in 100,000 live births. In certain instances, LNS is caused by a genetic deficiency of the enzyme hypoxanthine-guanine phosphoribosyltransferase (HGPRT). In certain instances, LNS is an X-linked recessive disease. In certain instances, LNS is present at birth in baby boys. In certain instances, the disease leads to severe gout, poor muscle control, and moderate mental retardation, which appear in the first year of life. In certain instances, the disease also results in self-mutilating behaviors (e.g., lip and finger biting, head banging) beginning in the second year of life. In certain instances, the disease also results in gout-like swelling in the joints and severe kidney problems. In certain instances, the disease leads neurological symptoms include facial grimacing, involuntary writhing, and repetitive movements of the arms and legs similar to those seen in Huntington's disease. The prognosis for individuals with LNS is poor. In certain instances, the life expectancy of an untreated individual with LNS is less than about 5 years. In certain instances, the life expectancy of a treated individual with LNS is greater than about 40 years of age.

In certain instances, hyperuricemia is found in individuals with cardiovascular disease (CVD) and/or renal disease. In certain instances, hyperuricemia is found in individuals with prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congestive heart failure, stroke, tumor lysis syndrome, endothelial dysfunction, oxidative stress, elevated renin levels, elevated endothelin levels, and/or elevated C-reactive protein levels. In certain instances, hyperuricemia is found in individuals with obesity (e.g., central obesity), high blood pressure, hyperlipidemia, and/or impaired fasting glucose. In certain instances, hyperuricemia is found in individuals with metabolic syndrome. In certain instances, gouty arthritis is indicative of an increased risk of acute myocardial infarction. In some embodiments, administration of a compound described herein to an individual are useful for decreasing the likelihood of a clinical event associated with a disease or condition linked to hyperuricemia, including, but not limited to, prehypertension, hypertension, increased proximal sodium reabsorption, microalbuminuria, proteinuria, kidney disease, obesity, hypertriglyceridemia, low high-density lipoprotein cholesterol, hyperinsulinemia, hyperleptinemia, hypoadiponectinemia, peripheral, carotid and coronary artery disease, atherosclerosis, congestive heart failure, stroke, tumor lysis syndrome, endothelial dysfunction, oxidative stress, elevated renin levels, elevated endothelin levels, and/or elevated C-reactive protein levels.

In some embodiments, a compound or compound form as described herein is administered to an individual suffering from a disease or condition requiring treatment with a diuretic. In some embodiments, a compound or compound form as described herein is administered to an individual suffering from a disease or condition requiring treatment with a diuretic, wherein the diuretic causes renal retention of urate. In some embodiments, the disease or condition is congestive heart failure or essential hypertension.

In some embodiments, administration of a compound or compound form as described herein to an individual is useful for improving motility or improving quality of life.

In some embodiments, administration of a compound or compound form as described herein to an individual is useful for treating or decreasing the side effects of cancer treatment.

In some embodiments, administration of a compound or compound form as described herein to an individual is useful for decreasing kidney toxicity of cis-platin.

In certain instances, gout is treated by lowering the production of uric acid. In certain instances, gout is treated by increasing the excretion of uric acid. In certain instances, gout is treated by URAT 1, xanthine oxidase, xanthine dehydrogenase, xanthine oxidoreductase, a purine nucleoside phosphorylase (PNP) inhibitor, a uric acid transporter (URAT) inhibitor, a glucose transporter (GLUT) inhibitor, a GLUT-9 inhibitor, a solute carrier family 2 (facilitated glucose transporter), member 9 (SLC2A9) inhibitor, an organic anion transporter (OAT) inhibitor, an OAT-4 inhibitor, or combinations thereof. In general, the goals of gout treatment are to i) reduce the pain, swelling and duration of an acute attack, and ii) prevent future attacks and joint damage. In certain instances, gout attacks are treated successfully using a combination of treatments. In certain instances, gout is one of the most treatable forms of arthritis.

i) Treating the Gout Attack.

In certain instances, the pain and swelling associated with an acute attack of gout can be addressed with medications such as acetaminophen, steroids, nonsteroidal anti-inflammatory drugs (NSAIDs), adrenocorticotropic hormone (ACTH) or colchicine. In certain instances, proper medication controls gout within 12 to 24 hours and treatment is stopped after a few days. In certain instances, medication is used in conjunction with rest, increased fluid intake, icepacks, elevation and/or protection of the affected area/s. In certain instances, the aforementioned treatments do not prevent recurrent attacks and they do not affect the underlying diseases of abnormal uric acid metabolism.

ii) Preventing Future Attacks.

In certain instances, reducing serum uric acid levels below the saturation level is the goal for preventing further gout attacks. In some cases, this is achieved by decreasing uric acid production (e.g. allopurinol), or increasing uric acid excretion with uricosuric agents (e.g. probenecid, sulfinpyrazone, benzbromarone).

In certain instances, allopurinol inhibits uric acid formation, resulting in a reduction in both the serum and urinary uric acid levels and becomes fully effective after 2 to 3 months.

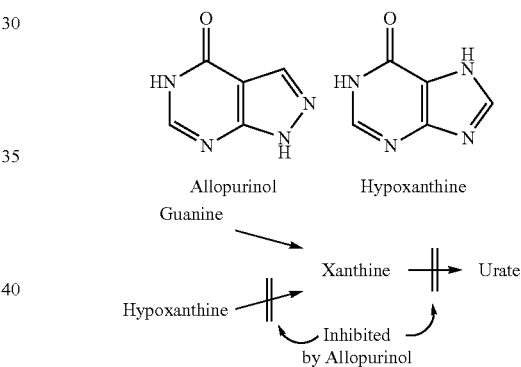

In certain instances, allopurinol is a structural analogue of hypoxanthine, (differing only in the transposition of the carbon and nitrogen atoms at positions 7 and 8), which inhibits the action of xanthine oxidase, the enzyme responsible for the conversion of hypoxanthine to xanthine, and xanthine to uric acid. In certain instances, it is metabolized to the corresponding xanthine analogue, alloxanthine (oxypurinol), which is also an inhibitor of xanthine oxidase. In certain instances, alloxanthine, though more potent in inhibiting xanthine oxidase, is less pharmaceutically acceptable due to low oral bioavailability. In certain instances, fatal reactions due to hypersensitivity, bone marrow suppression, hepatitis, and vasculitis have been reported with Allopurinol. In certain instances, the incidence of side effects may total 20% of all individuals treated with the drug. Treatment for diseases of uric acid metabolism has not evolved significantly in the following two decades since the introduction of allopurinol.

In certain instances, uricosuric agents (e.g., probenecid, sulfinpyrazone, and benzbromarone) increase uric acid excretion. In certain instances, probenecid causes an increase in uric acid secretion by the renal tubules and, when used chronically, mobilizes body stores of urate. In certain instances, 25-50% of individuals treated with probenecid fail to achieve reduction of serum uric acid levels <6 mg/dL. In certain instances, insensitivity to probenecid results from drug intolerance, concomitant salicylate ingestion, and renal impairment. In certain instances, one-third of the individuals develop intolerance to probenecid. In certain instances, administration of uricosuric agents also results in urinary calculus, gastrointestinal obstruction, jaundice and anemia.

Successful treatment aims to reduce both the pain associated with acute gout flare and long-term damage to the affected joints (Emerson, "The Management of Gout", *N Engl J Med.*, 334(7), 445-451, 1996). Therapeutic goals include providing rapid and safe pain relief, preventing further attacks, preventing the formation of tophi and subsequent arthritis, and avoiding exacerbating other medical conditions. Initiation of treatment depends upon the underlying causes of hyperuricemia, such as renal function, diet, and medications. While gout is a treatable condition, there are limited treatments available for managing acute and chronic gout and a number of adverse effects are associated with current therapies. Medication treatment of gout includes pain management, prevention or decrease in joint inflammation during an acute gouty attack, and chronic long-term therapy to maintain decreased serum uric acid levels.

Nonsteroidal anti-inflammatory drugs (NSAIDs) are effective anti-inflammatory medications for acute gout but are frequently associated with irritation of the gastrointestinal (GI) system, ulceration of the stomach and intestines, and occasionally intestinal bleeding (Schlesinger, "Management of Acute and Chronic Gouty Arthritis Present State-of-the-Art"; *Medications*; 64 (21), 2399-2416, 2004; Pascual and Sivera, "Therapeutic advances in gout"; *Curr Opin Rheumatol., March;* 19(2), 122-7, 2007). Colchicine for acute gout is most commonly administered orally as tablets (every 1-2 hours until there is significant improvement in pain or the patient develops GI side effects such as severe diarrhea, nausea and vomiting), or intravenously. Corticosteroids, given in short courses, can be administered orally or injected directly into the inflamed joint.

Medications are available for reducing blood uric acid levels that either increase renal excretion of uric acid by inhibiting re-uptake or reduce production of uric acid by blockade of xanthine oxidase. These medicines are generally not initiated until after the inflammation from acute gouty arthritis has subsided because they may intensify the attack. If they are already being taken prior to the attack, they are continued and only adjusted after the attack has resolved. Since many subjects with elevated blood uric acid levels may not develop gouty attacks or kidney stones, the decision for prolonged treatment with uric acid-lowering medications is individualized.

Kits

The compounds, compound forms, compositions and methods described herein provide kits for the treatment of diseases and disorders, such as the ones described herein. These kits comprise a compound, compound form, compounds, compound forms or compositions described herein in a container and, optionally, instructions teaching the use of the kit according to the various methods and approaches described herein. Such kits may also include information, such as scientific literature references, package insert materials, clinical trial results, and/or summaries of these and the like, which indicate or establish the activities and/or advantages of the composition, and/or which describe dosing, administration, side effects, drug interactions, or other information useful to the health care provider. Such information may be based on the results of various studies, for example, studies using experimental animals involving in vivo models and studies based on human clinical trials. Kits described herein can be provided, marketed and/or promoted to health providers, including physicians, nurses, pharmacists, formulary officials, and the like. Kits may also, in some embodiments, be marketed directly to the consumer.

The compounds, compound forms and pharmaceutical compositions described herein may be utilized for diagnostics and as research reagents. For example, the compounds, compound forms and pharmaceutical compositions, either alone or in combination with other compounds, can be used as tools in differential and/or combinatorial analyses to elucidate expression patterns of genes expressed within cells and tissues. As one non-limiting example, expression patterns within cells or tissues treated with one or more compounds are compared to control cells or tissues not treated with compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Besides being useful for human treatment, the compounds, compound forms and pharmaceutical compositions described herein are also useful for veterinary treatment of companion animals (e.g. dogs, cats), exotic animals and farm animals (e.g. horses), including mammals, rodents, and the like.

The examples and preparations provided below further illustrate and exemplify the compounds of the present invention and methods of preparing such compounds. It is to be understood that the scope of the present invention is not limited in any way by the scope of the following examples and preparations.

Lesinurad

Lesinurad is the generic name for 2-(5-bromo-4-(4-cyclopropylnaphthalen-1-yl)-4H-1,2,4-triazol-3-ylthio)acetic acid (formula I), whose chemical structure is:

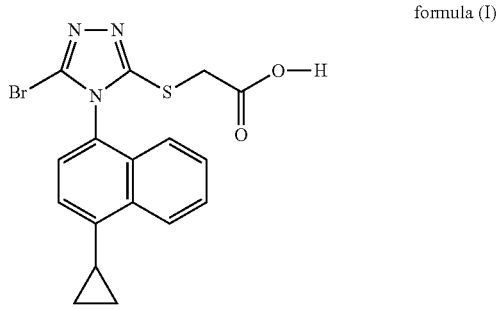 [SMILES: O=C(O)CSc1nnc(Br)n1-c1ccc(C2CC2)c2ccccc12]

formula (I)

In some instances, the term Lesinurad also includes the sodium salt of Lesinurad, i.e. sodium 2-(5-bromo-4-(4-cyclopropylnaphthalen-1-yl)-4H-1,2,4-triazol-3-ylthio)acetate. In the examples described herein, the compound administered may be Lesinurad, or its sodium salt, in an amorphous or polymorph form thereof. In instances where the sodium salt is used, the amounts quoted herein may in fact be lower than the actual amounts of the sodium salt of Lesinurad used in the experiment, but were calculated to provide an effective amount of the free acid compound.

EXAMPLES

Example 1

Phase II Clinical Trial—Gout Dose Response Study

Purpose: To compare the proportion of subjects whose serum urate (sUA) level is <6.0 mg/dL after 28 days of dosing by treatment group.

Official Title: Randomized, Double-Blind, Multicenter, Placebo-Controlled, Safety and Efficacy Study of Lesinurad Versus Placebo in the Treatment of Hyperuricemia in Patients With Gout Experimental Dosage Form: 200 mg capsule of Lesinurad, with appropriate pharmaceutically acceptable excipients Condition: Hyperuricemia
Intervention: Lesinurad or Placebo
Study Type: Interventional
Study: Allocation: Randomized
Design:
Control: Placebo Control
Endpoint Classification: Safety/Efficacy Study
Intervention Model: Parallel Assignment
Masking: Double Blind (Subject, Caregiver, Investigator, Outcomes Assessor)
Primary Purpose: Treatment
Primary Outcome Measures: Compare the proportion of subjects whose serum urate (sUA) level is <6.0 mg/dL after 28 days of dosing by treatment group.
Secondary Outcome Measures:
Evaluate the proportion of subjects with sUA levels <6.0 mg/dL at each weekly study visit.
Evaluate absolute and percent reduction from baseline in sUA levels at each weekly study visit.
Evaluate the percent change in 24-hr urine urate level (excretion) from baseline to Day 28.
Evaluate the incidence of gout flares.
Evaluate the safety and tolerability of Lesinurad in subjects with gout.

TABLE 1

Clinical Study Design

| Arm | Intervention |
| --- | --- |
| 1 | Lesinurad 200 mg qd for 28 days |
| 2 | Lesinurad 200 mg qd for 7 days followed by 400 mg qd for 21 days |
| 3 | Lesinurad 200 mg qd for 7 days, followed by 400 mg qd for 7 days, followed by 600 mg qd for 14 days |
| 4 | Matching placebo qd for 28 days |

Eligibility
Ages Eligible for Study: 18-75 Years
Genders Eligible for Study: Both
Accepts Healthy Volunteers: No
Inclusion Criteria:
Male or post-menopausal or surgically sterile female.
Hyperuricemic (i.e., screening sUA ≥8 mg/dL).
Meets criteria for the diagnosis of gout as per the American Rheumatism Association (ARA) Criteria for the Classification of Acute Arthritis of Primary Gout (see Appendix B).
Willing and able to give informed consent and adhere to visit/protocol schedules (informed consent must be given before the first study procedure is performed).
Exclusion Criteria:
Classified as an overproducer of urine urate (Cur >6.0 ml/min/1.73 m² 24-hour urine).
Consumes more than 14 drinks of alcohol per week (e.g., 1 drink=5 oz [150 ml] of wine, 12 oz [360 ml] of beer, or 1.5 oz [45 ml] of hard liquor).
History or suspicion of drug abuse.
Documented history of, or suspicion of, kidney stones.
History of rheumatoid arthritis or other autoimmune disease.
Confirmed (positive serology to HIV1 and HIV2) or suspected HIV infection.
Positive serology to HCV antibodies (Abs), and/or hepatitis B surface antigen (HBsAg).
History of malignancy, except treated non-melanomatous skin cancer or cervical dysplasia.
History of cardiac abnormalities, including abnormal and clinically relevant ECG changes such as bradycardia (sinus rate <45 bpm), complete left bundle branch block (LBBB), second or third degree heart block, intraventricular conduction delay with QRS duration >120 msec, symptomatic or asymptomatic arrhythmias with the exception of sinus arrhythmia, evidence of ventricular pre-excitation, frequent palpitations or syncopal episodes, heart failure, hypokalemia, family history of Long QT Syndrome, and/or family history of sudden death in an otherwise healthy individual between the ages of 1 and 30 years.
Any condition predisposing them to QT prolongation including pathological Q-wave (defined as Q-wave >40 msec or depth >0.4-0.5 mV).
Any use of a concomitant medication that prolong the QT/QTc interval within the 14 days prior to Baseline (Day 0).
QT interval corrected for heart rate according to Fridericia (QTcF)>450 msec at Screening or pre-dose at Baseline (Day 0).
Uncontrolled hypertension (above 150/95).
Inadequate renal function [serum creatinine >1.5 mg/dL or creatinine clearance <60 mL/min (by Cockroft-Gault formula)].
Hemoglobin <10 g/dL (males) or <9 g/dL (females).
Alanine aminotransferase (ALT) or aspartate aminotransferase (AST)>2.5×upper limit of normal (ULN).
Gamma glutamyl transferase (GGT)>3×ULN.
Active peptic ulcer disease requiring treatment.
History of xanthinuria, active liver disease, or hepatic dysfunction.
Requires therapy with any other urate-lowering medication, other than the study medication.
Requires long-term use of salicylates; diuretics; azathioprine; mercaptopurine; theophylline; intravenous colchicine; cyclosporine; cyclophosphamide; pyrazinamide; sulfamethoxazole; or trimethoprim.
Taking medications known as enzyme inducers.
Gout flare at screening that is resolved for less than one week prior to the first treatment with study medication (exclusive of chronic synovitis/arthritis).
Pregnant or breast feeding.
Received an investigational medication within 4 weeks prior to study medication administration.
Known hypersensitivity or allergy to colchicine or any components in their formulations.
Body mass index (BMI)>40 kg/m².
Taking greater than 1000 mg/day of Vitamin C.
Any other medical or psychological condition, which in the opinion of the Investigator and/or Medical Monitor, might create undue risk to the subject or interfere with the subject's ability to comply with the protocol requirements, or to complete the study.
Results: Incidence of gout flares are presented in Table 2 below indicating the majority of flares occurred in the first week when patients were receiving 200 mg QD (6/10 total flares on drug). Few additional flares occurred as dose increased, even with greater decrease in sUA. Duration of flares is shorter at higher doses, the opposite of what would be expected with greater reduction in sUA.

TABLE 2

Incidence of Gout Flares

| Randomized Dose Group | N | % Patients with Flares | Mean Duration of Flares | % of patients with Flares by Dose at Time of Flare | Mean Duration of Flares |
|---|---|---|---|---|---|
| 600 mg | 32 | 13% | 1.5 days | 9% (3/32) | 1.7 days |
| 400 mg | 33 | 12% | 3.8 days | 2% (1/65) | 2 days |
| 200 mg | 31 | 6% | 4 days | 6% (6/96) | 4 days |
| Placebo | 27 | 4% | 1 day | 4% | 1 day |

Example 2

Figure 2:
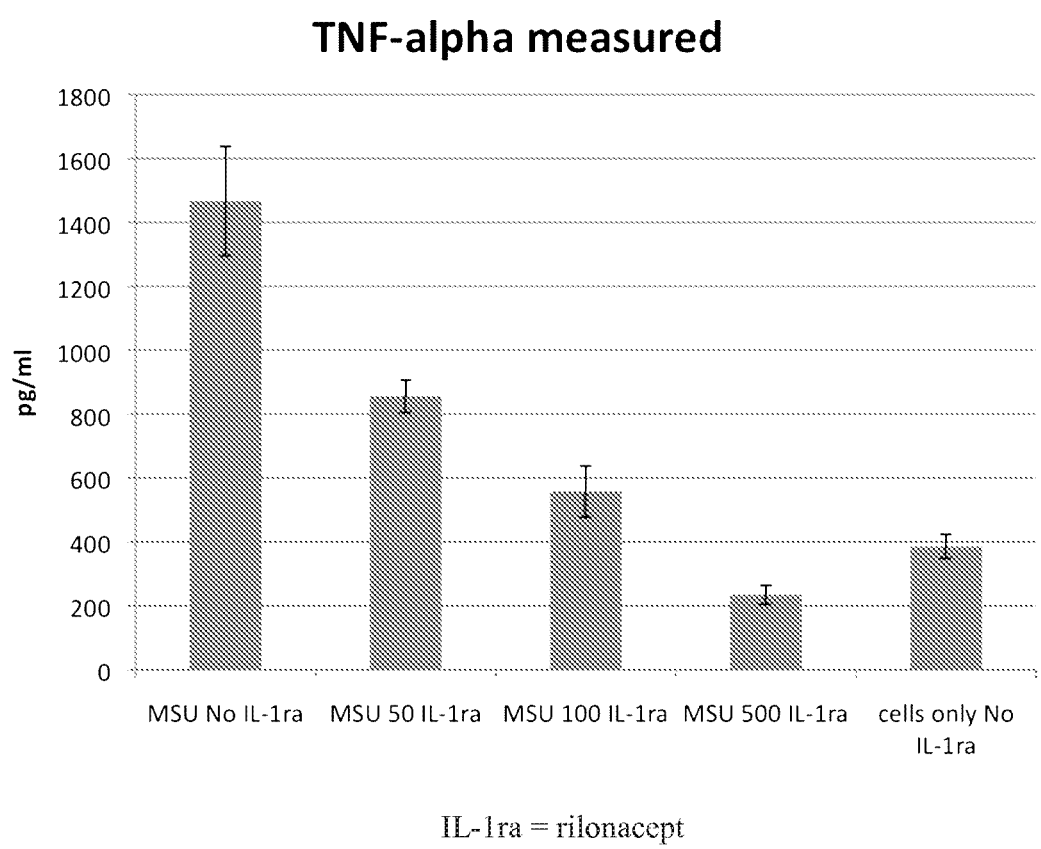
FIG. 2 illustrates the effect of rinolacept on TNF-a production.
Figure 3:
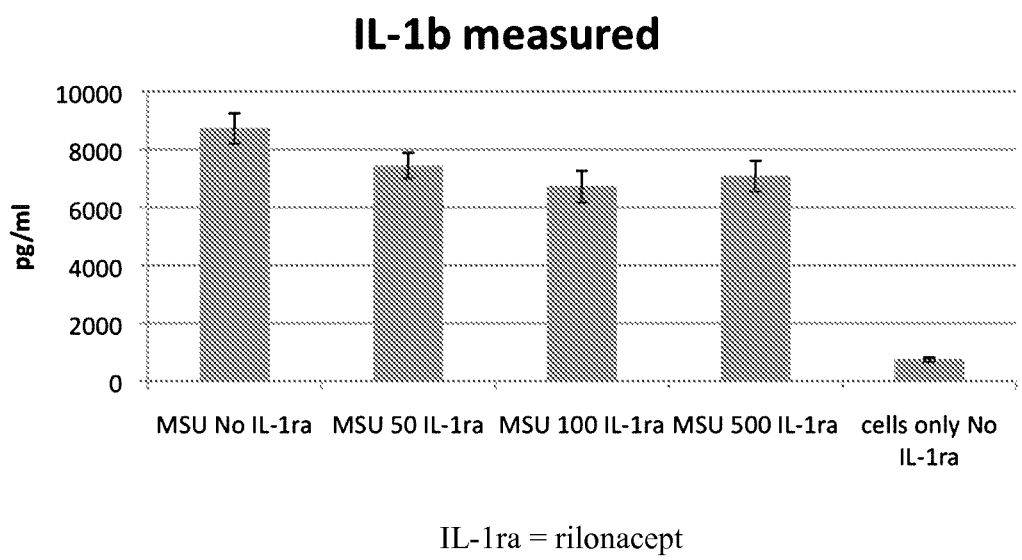
FIG. 3 illustrates the effect of rinolacept on IL-1 production.

Comparison of 2-(5-bromo-4-(4-cyclopropylnaphthalen-1-yl)-4H-1,2,4-triazol-3-ylthio)acetate sodium salt to other gout therapies Activation of the inflammasome results in the release of preformed IL-1 which goes on to activate other targets as well as increase the production of IL-1 itself 2-(5-Bromo-4-(4-cyclopropylnaphthalen-1-yl)-4H-1,2,4-triazol-3-ylthio)acetate sodium salt (compound 1 or cmpd1) blocks IL-1 release very early, within 1 hour of stimulation, as illustrated in FIG. 1. This activity may be compareded with rilonacept which only inhibits the production of TNF-α, (as expected since TNF-α production is downstream of IL-1b action) as illustrated in FIG. 2 (6 hour time point). However, rilonacept does not reduce IL-1 production as illustrated in FIG. 3.

Example 3

Evaluation of anti-inflammatory activity of 2-(5-bromo-4-(4-cyclopropylnaphthalen-1-yl)-4H-1,2,4-triazol-3-ylthio)acetate sodium salt in a rat air pouch model of crystal-induced arthropathy Procedures:
1. Preparation of MSU crystals.
   a. 1.68 g uric acid was dissolved in 500 ml 0.01 NaOH and heated to 70° C. NaOH was added as required to maintain pH between 8-9. The solution was filtered and incubated at ambient with slow stirring continuously for 24 hours.
   b. Crystals were washed, dried and sterilized by autoclaving.
   c. Crystals were suspended in sterile saline at 0.67 mg/ml, 2.67 mg/ml and 10 mg/ml just prior to use.
2. 110 Sprague-Dawley rats (male, 160-180 g) were obtained. Following quarantine, rats were accepted for the Study if no signs of clinical distress were noted during the 3-day quarantine period. The rats were maintained on certified laboratory diet and water ad libitum.
3. The rats were ear-notched for individual identification.
4. The rat weights were recorded.
5. The rats were distributed randomly to 11 groups of 10 rats per group based upon average weight.
6. The rats were anesthetized and bled for sample from retro-orbital sinus into microtainer tubes.
   a. The blood was processed to serum;
   b. The serum was transferred to labeled Eppendorf tubes (T=0) and stored at −80° C.
   c. Minimum serum volume of 100 µl (or 200 µl blood) was collected from each rat.
7. DAY 0: The rats are anesthetized.
   a. The nape of the neck was shaved, cleansed with 70% isopropanol followed by cleansing with Povidone.
   b. A 23-gauge needle was attached to a 30 ml syringe fitted with an air filter.
   c. 30 ml of sterile air was injected subcutaneously and the rat returned to routine maintenance.
8. DAY 3: Steps 7a) through 7c) were repeated.
9. DAYS 4 and 5:
   a. Rats in test compound groups were dosed once daily by subcutaneous injection or oral dosing as in TABLE 3.
   b. 24 hours after dosing on DAY 4 (DAY 5), sample bleeds are collected from each rat immediately prior to dosing on DAY 5, processed to serum and stored at −80° C. A minimum of 0.100 ml serum was collected for each bleed.
10. DAY 6: TIME=0 HOUR: Rats were injected subcutaneously with Colchicine or dosed orally with Vehicle, Test Compound 1 (2-(5-bromo-4-(4-cyclopropylnaphthalen-1-yl)-4H-1,2,4-triazol-3-ylthio)acetate sodium salt) or Test Compound Allopurinol.
    Test compound 1 formulation: 2-(5-bromo-4-(4-cyclopropylnaphthalen-1-yl)-4H-1,2,4-triazol-3-ylthio)acetate sodium salt was dissolved in distilled water (dH$_2$O) to prepare a 20 mg/ml dosing solution (Group 10). The 20 mg/ml stock was diluted in dH$_2$O to prepare a 6 mg/ml solution (Group 9) and a 2 mg/ml solution (Group 8).
    Allopurinol formulation: Allopurinol was dissolved in distilled water (dH$_2$O) to prepare a 2 mg/ml dosing solution (Group 11).
    Immediately following SC injections, each animal was injected intravenously with Evans blue dye (2.5% w/vol; 2.0 ml/kg). Evans blue binds to albumin and acts as a marker for plasma extravasation.
11. Treatments.

TABLE 3

GROUP TREATMENTS

| Group | No. Rats | Treatment | Dose (mg/kg) | ROA | Timing | MSU (mg) |
|---|---|---|---|---|---|---|
| 1 | 10 | Vehicle | N/A | PO | 30 min | None |
| 2 | 10 | Vehicle | N/A | PO | 30 min | 10 |
| 3 | 10 | Vehicle | N/A | PO | 30 min | 40 |
| 4 | 10 | Vehicle | N/A | PO | 30 min | 150 |
| 5 | 10 | Colchicine | 0.01 | SC | 30 min | 150 |
| 6 | 10 | Colchicine | 0.1 | SC | 30 min | 150 |
| 7 | 10 | Colchicine | 1 | SC | 30 min | 150 |
| 8 | 10 | Cmpd1 | 10 | PO | 30 min | 150 |
| 9 | 10 | Cmpd1 | 30 | PO | 30 min | 150 |
| 10 | 10 | Cmpd1 | 100 | PO | 30 min | 150 |
| 11 | 10 | Allopurinol | 10 | PO | 30 min | 150 |

12. Thirty minutes after treatment, the rats were anesthetized and injected into the air pouch with 15 ml MSU suspension.
13. Four (4) hours after MSU injection, the rats were anesthetized and bled for sample from retro-orbital sinus into microtainer tubes.
    a. The blood was processed to serum
    b. The serum was transferred to labeled Eppendorf tubes (T=0) and stored at −80° C.
    c. Minimum serum volume of 100 µl (or 200 µl blood) was collected from each rat.
    d. 5 ml of sterile PBS containing 10 U/ml heparin was injected into the air pouch of anesthetized rats.
       1) The pouch was gently massaged and the exudate was immediately removed from the air pouch. Exudates volume was measured and recorded for each animal.
          a. Exudate cells were collected by centrifugation at 2,000 rpm for 5 minutes at room temperature. The supernatants were aliquoted to two portions and stored at −80° C.
          b. Cells were re-suspended in 0.5 ml heparinized saline for neutrophil cell counts.

c. Plasma extravasation was measured by optical absorbance at 620 nm for each exudate sample.
14. Exudate from each animal was assayed for TNF-alpha and IL-1.
15. Data treatments:
   a. Mean cell counts and standard deviations were determined for each group.
   b. Mean optical absorbance measurements and standard deviations were determined for each group.
   c. Group means and standard deviations for TNF-alpha and IL-1 were determined for each group.
   d. Statistical significance of treatments on mean cell counts, mean optical absorbance measurements and mean cytokine measurements were determined by comparison of means for treatment and positive control groups with vehicle group.

Figure 4:
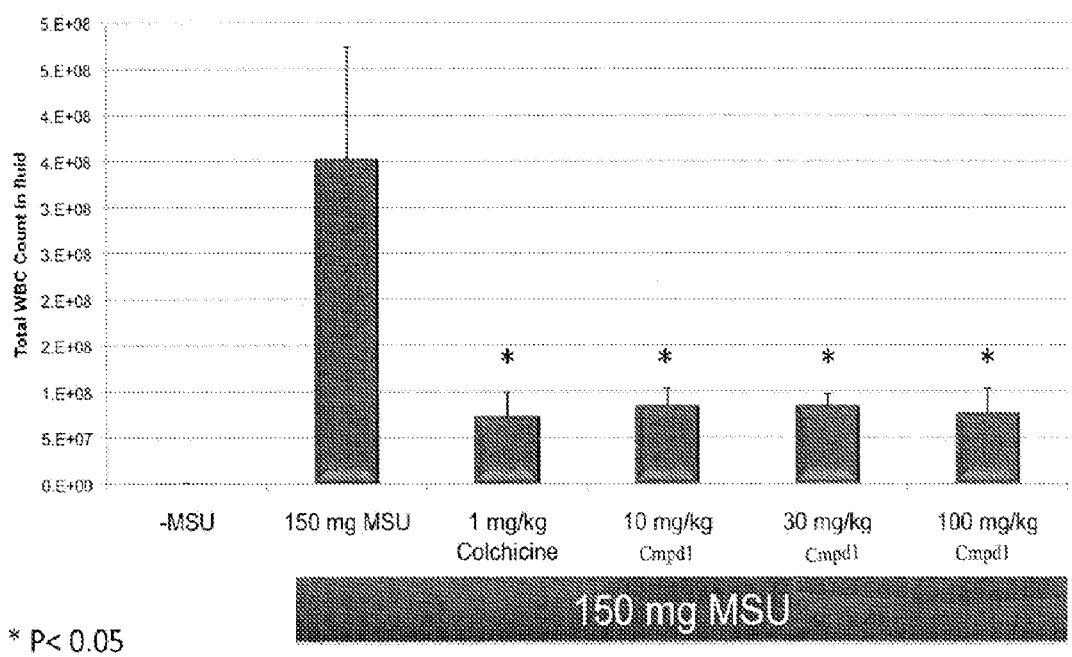
FIG. 4 illustrates the effect of compound 1 in a rat model of inflammation.
Figure 5:
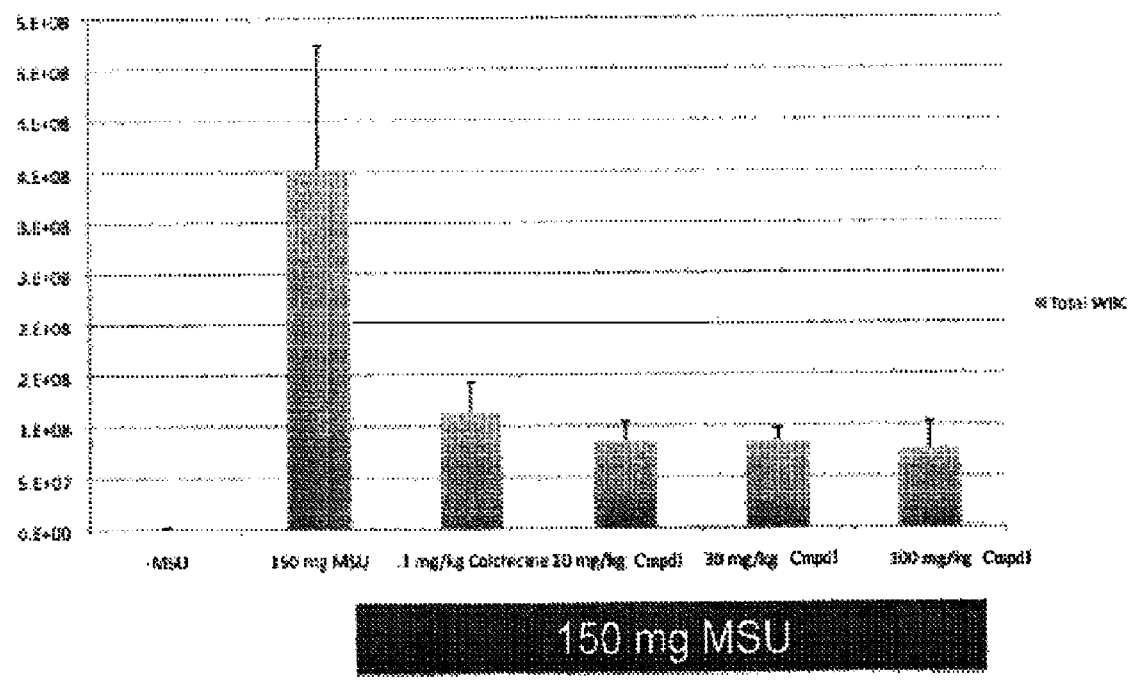
FIG. 5 illustrates the effect of compound 1 in a rat model of inflammation.

Conclusions:

As shown in FIGS. 4 and 5, monosodium urate crystal-induced inflammatory response was blocked by compound 1. FIG. 4 provides the comparison with 1 mg/kg colchicine and FIG. 5 provides the comparison with 0.1 mg/kg colchicine.

Example 4

Figure 6:
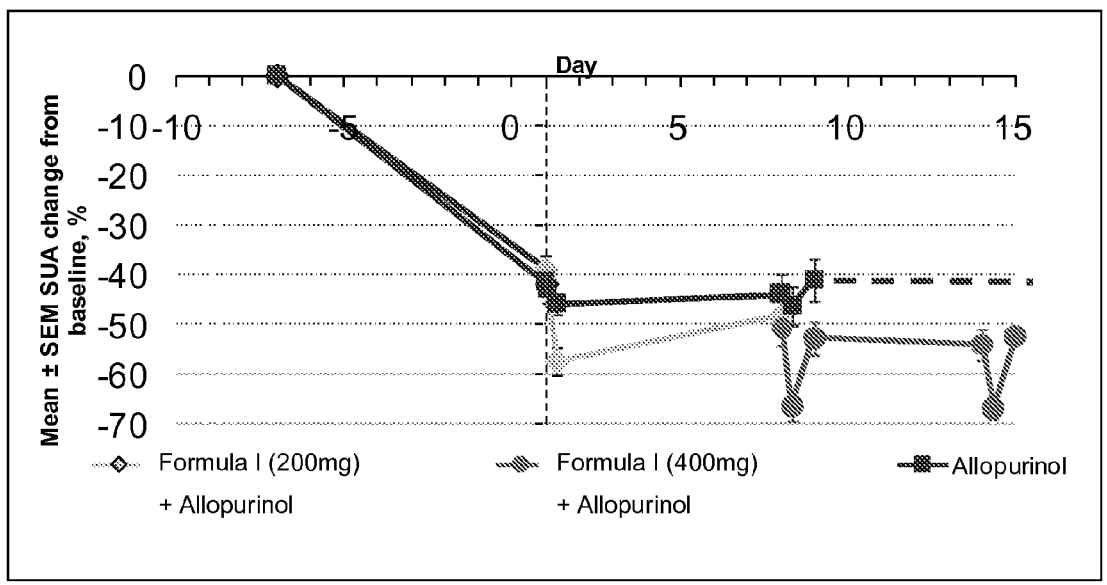
FIG. 6 illustrates the effect of compound of formula I in combination with allopurinol is greater than compound of formula I alone. (Dotted line indicates last observation carried forward for days 10-15 for allopurinol alone.)

A: Patients received allopurinol 300 mg QD for 1 week followed by a compound of Formula I. A compound of Formula I (200 mg) reduced serum uric acid levels 9% beyond the reduction observed for allopurinol alone. Titration up to 400 mg of a compound of Formula I provided further reduction of serum uric acid levels by 6%. The combination of a compound of Formula I (400 mg) and allopurinol provided 100% response (i.e., sUA <6 mg/dL) and an 80% sUA reduction below 5 mg/dL. These responses are illustrated in FIG. 6.

Figure 7:
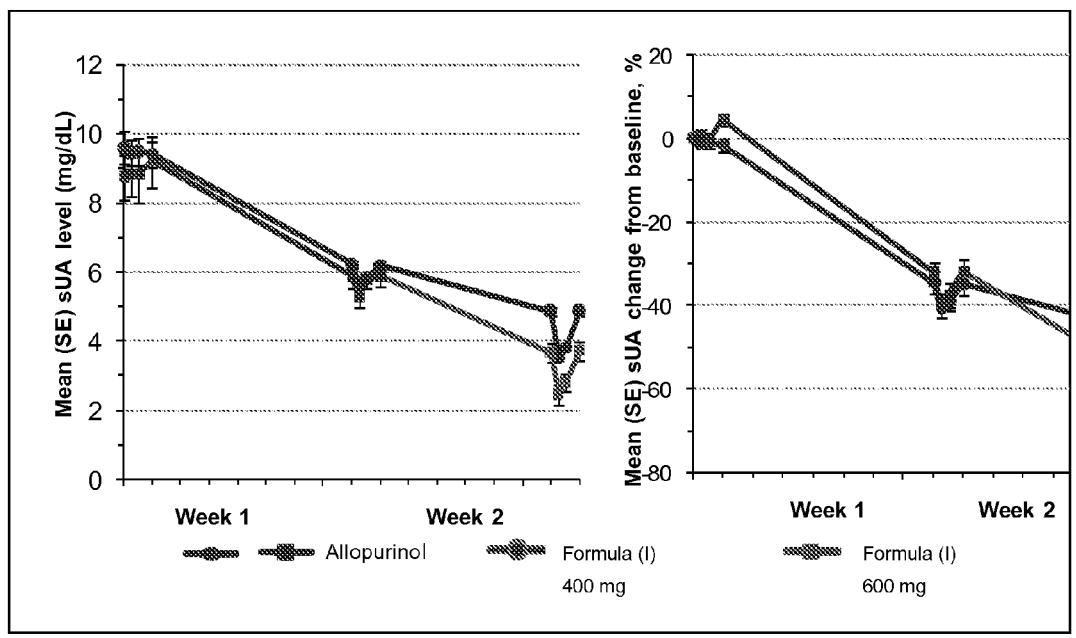
FIG. 7 illustrates compound of Formula I and allopurinol combination reduces sUA greater than allopurinol alone.

B: Patients received allopurinol alone for one week. For the second week, Panel 1 received a compound of Formula I (400 mg) and Panel 2 received a compound of Formula I (600 mg) in combination with allopurinol 300 mg. Combination therapy responses are illustrated in FIG. 7 and described in the table below:

| sUA | Allopurinol Alone | Formula I 400 mg + Allopurinol | Formula I 600 mg + Allopurinol |
| --- | --- | --- | --- |
| Mean % Reduction | 32 | 45 | 58 |
| Response: % Patients <6 mg/dL | 63 | 100 | 100 |
| % Patients <5 mg/dL | 9 | 67 | 100 |
| % Patients <4 mg/dL | 0 | 0 | 60 |

Example 5

Multiple-dose, placebo-controlled study in healthy volunteers designed to evaluate the sUA lowering effects, PK drug-drug interaction potential, safety and tolerability of Formula I in combination with febuxostat. Panel 1 received Formula I (200 mg) and Panel 2 received Formula I (400 mg), both alone and in combination with febuxostat 40 mg. The combination of a compound of Formula I with febuxostat resulted in approximately a 70% mean reduction in sUA levels compared to baseline, with intraday reductions over 80%, reaching mean sUA levels of 1.2 mg/dL. The results are illustrated in FIG. 8.

Example 6

Combination of 2-(5-bromo-4-(4-cyclopropylnaphthalen-1-yl)-4H-1,2,4-triazol-3-ylthio)acetate and Febuxostat This 21-patient, open-label, clinical pharmacology study included 2 cohorts of gout patients with sUA greater than 8 mg/dL on no urate-lowering therapy. All patients received colchicine beginning one week prior to baseline and continuing for 5 weeks for flare prophylaxis. The first cohort of patients in the study consisted of 12 gout patients with a median baseline sUA of 9.2 mg/dL who were administered 40 mg febuxostat for the first week, 40 mg febuxostat in combination with 400 mg 2-(5-bromo-4-(4-cyclopropylnaphthalen-1-yl)-4H-1,2,4-triazol-3-ylthio)acetate for the second week, and then 40 mg febuxostat in combination with 600 mg 2-(5-bromo-4-(4-cyclopropylnaphthalen-1-yl)-4H-1,2,4-triazol-3-ylthio)acetate for the third week. This sequence was repeated with 80 mg febuxostat in a second cohort of 9 patients who had a median baseline sUA of 10.4 mg/dL. As shown in the tables below, 100 percent of patients receiving the combination of 2-(5-bromo-4-(4-cyclopropylnaphthalen-1-yl)-4H-1,2,4-triazol-3-ylthio)acetate and febuxostat achieved serum urate (or "sUA") levels below the clinically important target of 6 mg/dL, compared to 67 percent and 56 percent for 40 mg and 80 mg, respectively, of febuxostat alone. At the highest combination doses tested (600 mg of 2-(5-bromo-4-(4-cyclopropylnaphthalen-1-yl)-4H-1,2,4-triazol-3-ylthio)acetate and 80 mg of febuxostat), 100 percent of patients also reached sUA levels below 4 mg/dL, with 58 percent achieving levels below 3 mg/dL. No patient achieved these reduced sUA levels on either dose of febuxostat alone. The combination of 2-(5-bromo-4-(4-cyclopropylnaphthalen-1-yl)-4H-1,2,4-triazol-3-ylthio)acetate and febuxostat was synergistic, with the addition of 600 mg 2-(5-bromo-4-(4-cyclopropylnaphthalen-1-yl)-4H-1,2,4-triazol-3-ylthio) acetate producing additional 39 and 51 percent reductions compared to 40 mg and 80 mg febuxostat alone, respectively. At the highest combination doses in cohorts one and two, patients achieved intraday median sUA levels of 2.4 mg/dL and 2.0 mg/dL, respectively. These levels of sUA reduction suggest the combination of 2-(5-bromo-4-(4-cyclopropylnaphthalen-1-yl)-4H-1,2,4-triazol-3-ylthio)acetate and febuxostat may be particularly useful in patients who have accumulated large deposits of uric acid, or tophi. In these patients, the substantial reduction of sUA, coupled with increased excretion of uric acid associated with 2-(5-bromo-4-(4-cyclopropylnaphthalen-1-yl)-4H-1,2,4-triazol-3-ylthio)acetate URAT1 mechanism, may lead to improved resolution of these tophi.

No clinically relevant drug interactions were observed between 2-(5-bromo-4-(4-cyclopropylnaphthalen-1-yl)-4H-1,2,4-triazol-3-ylthio)acetate and febuxostat. The combination of 2-(5-bromo-4-(4-cyclopropylnaphthalen-1-yl)-4H-1,2,4-triazol-3-ylthio)acetate and febuxostat was well tolerated, with no serious adverse events or discontinuations due to adverse events. There were no Grade 2 or higher increases in serum creatinine on 2-(5-bromo-4-(4-cyclopropylnaphthalen-1-yl)-4H-1,2,4-triazol-3-ylthio)acetate alone or the combination with febuxostat, but one Grade 2 serum creatinine increase occurred on colchicine alone. There was one Grade 3 increase in the liver enzyme, alanine aminotransferase (ALT), on febuxostat 40 mg alone, which normalized during combination treatment with 2-(5-bromo-4-(4-cyclopropylnaphthalen-1-yl)-4H-1,2,4-triazol-3-ylthio)acetate.

Cohort 1: Response Rates and Median Percent Changes from Baseline (Median Baseline = 9.2 mg/dL) in Gout Patients for 40 mg Febuxostat Monotherapy and in Combination with 400 mg or 600 mg 2-(5-bromo-4-(4-cyclopropylnaphthalen-1-yl)-4H-1,2,4-triazol-3-ylthio)acetate

| | Febuxostat 40 mg alone | Febuxostat (40 mg) and 2-(5-bromo-4-(4-cyclopropyl-naphthalen-1-yl)-4H-1,2,4-triazol-3-ylthio)acetate (400 mg) | Febuxostat (40 mg) and 2-(5-bromo-4-(4-cyclopropyl-naphthalen-1-yl)-4H-1,2,4-triazol-3-ylthio)acetate (600 mg) |
|---|---|---|---|
| Response rate (<6 mg/dL) | 67% | 100% | 100% |
| Percent patients <4 mg/dL | 0% | 50% ($P < 0.05$) | 64% ($P < 0.01$) |
| Percent sUA change at trough | −35% | −56% ($P < 0.001$) | −61% ($P < 0.001$) |
| Percent sUA change intraday | −44% | −68% ($P < 0.001$) | −71% ($P < 0.001$) |

Cohort 2: Response Rates and Median Percent Changes from Baseline (Median Baseline = 10.4 mg/dL) in Gout Patients for 80 mg Febuxostat Monotherapy and in Combination with 400 mg or 600 mg 2-(5-bromo-4-(4-cyclopropylnaphthalen-1-yl)-4H-1,2,4-triazol-3-ylthio)acetate

| | Febuxostat 80 mg alone | Febuxostat (80 mg) and 2-(5-bromo-4-(4-cyclopropyl-naphthalen-1-yl)-4H-1,2,4-triazol-3-ylthio)acetate (400 mg) | Febuxostat (80 mg) and 2-(5-bromo-4-(4-cyclopropyl-naphthalen-1-yl)-4H-1,2,4-triazol-3-ylthio)acetate (600 mg) |
|---|---|---|---|
| Response rate (<6 mg/dL) | 56% | 100% ($P < 0.05$) | 100% ($P < 0.05$) |
| Percent patients <4 mg/dL | 0% | 89% ($P < 0.001$) | 100% ($P < 0.001$) |
| Percent sUA change at trough | −47% | −65% ($P < 0.001$) | −73% ($P < 0.001$) |
| Percent sUA change intraday | −52% | −78% ($P < 0.001$) | −81% ($P < 0.001$) |

Example 7

Combination of 2-(5-bromo-4-(4-cyclopropylnaphthalen-1-yl)-4H-1,2,4-triazol-3-ylthio)acetate and Allopurinol This 20-patient, open-label clinical pharmacology study included 2 cohorts of gout patients with sUA greater than 8 mg/dL on no urate-lowering therapy who began colchicine dosing one week prior to baseline and continued for 5 weeks. The first cohort of 10 patients with a median baseline sUA of 9.8 mg/dL received 300 mg allopurinol alone for the first week, then 300 mg allopurinol plus 400 mg 2-(5-bromo-4-(4-cyclopropylnaphthalen-1-yl)-4H-1,2,4-triazol-3-ylthio) acetate for the second week, followed by 400 mg 2-(5-bromo-4-(4-cyclopropylnaphthalen-1-yl)-4H-1,2,4-triazol-3-ylthio)acetate alone for the third week. In the second cohort, 10 patients with a median baseline sUA of 9.1 mg/dL followed the same dosing scheme for the same time period at a dose of 300 mg allopurinol and 600 mg 2-(5-bromo-4-(4-cyclopropylnaphthalen-1-yl)-4H-1,2,4-triazol-3-ylthio)acetate. As shown in the tables below, 100 percent of patients receiving all combinations of 2-(5-bromo-4-(4-cyclopropylnaphthalen-1-yl)-4H-1,2,4-triazol-3-ylthio)acetate and allopurinol achieved sUA reductions to below the 6 mg/dL target. On 300 mg allopurinol alone, only 20 percent of patients achieved target sUA levels below 6 mg/dL. On 600 mg 2-(5-bromo-4-(4-cyclopropylnaphthalen-1-yl)-4H-1,2,4-triazol-3-ylthio)acetate alone, 67 percent of patients achieved sUA levels below 6 mg/dL, which was significantly better than allopurinol alone (p<0.05). At the highest combination doses tested, 90 percent of patients also reached sUA levels below 5 mg/dL, and 50 percent reached levels below 4 mg/dL. At the highest combination doses tested, intraday median sUA levels below 3 mg/dL were achieved. No clinically relevant drug interactions were observed between 2-(5-bromo-4-(4-cyclopropylnaphthalen-1-yl)-4H-1,2,4-triazol-3-ylthio)acetate and allopurinol in this study; however, plasma levels of oxypurinol, an active metabolite of allopurinol, were decreased approximately 25-35 percent. Despite this small decrease, the combination of 600 mg 2-(5-bromo-4-(4-cyclopropylnaphthalen-1-yl)-4H-1,2,4-triazol-3-ylthio)acetate and allopurinol demonstrated a completely additive response. The combination of 2-(5-bromo-4-(4-cyclopropylnaphthalen-1-yl)-4H-1,2,4-triazol-3-ylthio)acetate and allopurinol was well tolerated. There were no serious adverse events or discontinuations that were considered possibly related to 2-(5-bromo-4-(4-cyclopropylnaphthalen-1-yl)-4H-1,2,4-triazol-3-ylthio)acetate or the combination. There were no clinically relevant increases in serum creatinine or ALT in this study. Two patients receiving 2-(5-bromo-4-(4-cyclopropylnaphthalen-1-yl)-4H-1,2,4-triazol-3-ylthio)acetate and colchicine had Grade 4 increases in creatine kinase (CK); one of these, although asymptomatic, was considered to be rhabdomyolysis by the investigator. Both cases were considered possibly related to colchicine and not related to 2-(5-bromo-4-(4-cyclopropylnaphthalen-1-yl)-4H-1,2,4-triazol-3-ylthio)acetate. Elevations in CK and rhabdomyolysis are known side effects of colchicine. One of these patients was also receiving a statin, which is also known to cause CK elevations, particularly when combined with colchicine.

Cohort 1: Response Rates and Median Percent Changes from Baseline (Median Baseline = 9.8 mg/dL) in Gout Patients for 300 mg Allopurinol Monotherapy, in Combination with 400 mg 2-(5-bromo-4-(4-cyclopropylnaphthalen-1-yl)-4H-1,2,4-triazol-3-ylthio)acetate, and 400 mg 2-(5-bromo-4-(4-cyclopropylnaphthalen-1-yl)-4H-1,2,4-triazol-3-ylthio)acetate monotherapy

| | Allopurinol (300 mg) alone | Allopurinol (300 mg) and 2-(5-bromo-4-(4-cyclopropyl-naphthalen-1-yl)-4H-1,2,4-triazol-3-ylthio)acetate (400 mg) | 2-(5-bromo-4-(4-cyclopropyl-naphthalen-1-yl)-4H-1,2,4-triazol-3-ylthio)acetate (400 mg) alone |
|---|---|---|---|
| Response rate (<6 mg/dL) | 10% | 100% ($P < 0.001$) | 20% |
| Percent patients <5 mg/dL | 5% | 50% ($P < 0.01$) | 0% |
| Percent sUA change at trough | −31% | −45% ($P < 0.001$) | −28% |

Cohort 1: Response Rates and Median Percent Changes from Baseline (Median Baseline = 9.8 mg/dL) in Gout Patients for 300 mg Allopurinol Monotherapy, in Combination with 400 mg 2-(5-bromo-4-(4-cyclopropylnaphthalen-1-yl)-4H-1,2,4-triazol-3-ylthio)acetate, and 400 mg 2-(5-bromo-4-(4-cyclopropylnaphthalen-1-yl)-4H-1,2,4-triazol-3-ylthio)acetate monotherapy

|  | Allopurinol (300 mg) alone | Allopurinol (300 mg) and 2-(5-bromo-4-(4-cyclopropyl-naphthalen-1-yl)-4H-1,2,4-triazol-3-ylthio)acetate (400 mg) | 2-(5-bromo-4-(4-cyclopropyl-naphthalen-1-yl)-4H-1,2,4-triazol-3-ylthio)acetate (400 mg) alone |
| --- | --- | --- | --- |
| Percent sUA change intraday | −38% | −62% ($P < 0.001$) | −44% ($P < 0.05$) |

Cohort 2: Response Rates and Median Percent Changes from Baseline (Median Baseline = 9.1 mg/dL) in Gout Patients for 300 mg Allopurinol Monotherapy, in Combination with 600 mg 2-(5-bromo-4-(4-cyclopropylnaphthalen-1-yl)-4H-1,2,4-triazol-3-ylthio)acetate, and 600 mg 2-(5-bromo-4-(4-cyclopropylnaphthalen-1-yl)-4H-1,2,4-triazol-3-ylthio)acetate monotherapy

|  | Allopurinol (300 mg) alone | Allopurinol (300 mg) and 2-(5-bromo-4-(4-cyclopropyl-naphthalen-1-yl)-4H-1,2,4-triazol-3-ylthio)acetate (600 mg) | 2-(5-bromo-4-(4-cyclopropyl-naphthalen-1-yl)-4H-1,2,4-triazol-3-ylthio)acetate (600 mg) alone |
| --- | --- | --- | --- |
| Response rate (<6 mg/dL) | 30% | 100% ($P < 0.001$) | 67% ($P < 0.05$) |
| Percent patients <5 mg/dL | 5% | 90% ($P < 0.001$) | 33% |
| Percent sUA change at trough | −27% | −55% ($P < 0.001$) | −39% ($P < 0.01$) |
| Percent sUA change intraday | −35% | −70% ($P < 0.001$) | −54% ($P < 0.001$) |

What is claimed is:

1. A method of reducing serum uric acid levels, treating hyperuricemia, or treating gout in a human comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to the human, wherein said method provides serum urate levels of less than 6 mg/dL; and wherein said method results in an adverse event in less than 15% of the humans.

2. A method of reducing serum uric acid levels, treating hyperuricemia, or treating gout in a human comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to the human, wherein the serum urate levels are less than 4 mg/dL.

3. A method of reducing serum uric acid levels, treating hyperuricemia, or treating gout in a human comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to the human, wherein said method provides serum urate levels of less than 6 mg/dL; and wherein the method provides a serum urate levels intraday change from baseline of more than 50%.

4. A method of reducing serum uric acid levels, treating hyperuricemia, or treating gout in a human comprising co-administration of 2-(5-bromo-4-(4-cyclopropylnaphthalen-1-yl)-4H-1,2,4-triazol-3-ylthio)acetate, or a pharmaceutically acceptable salt thereof, and allopurinol to the human, wherein said method provides serum urate levels of less than 6 mg/dL, wherein the gout in the human is characterized by the presence of large accumulated deposits of uric acid or tophi.

* * * * *